United States Patent
Pellerin et al.

(10) Patent No.: US 7,276,373 B2
(45) Date of Patent: Oct. 2, 2007

(54) SURROGATE CELL-BASED SYSTEM AND METHOD FOR ASSAYING THE ACTIVITY OF HEPATITIS C VIRUS NS3 PROTEASE

(75) Inventors: Charles Pellerin, Laval (CA); Daniel Lamarre, Terrebonne (CA)

(73) Assignee: Boehringer Ingelheim (Canada) Ltd., Laval (CA)

( * ) Notice: Subject to any disclaimer, the term of this patent is extended or adjusted under 35 U.S.C. 154(b) by 526 days.

(21) Appl. No.: 10/328,206

(22) Filed: Dec. 23, 2002

(65) Prior Publication Data

US 2003/0162169 A1 Aug. 28, 2003

Related U.S. Application Data

(63) Continuation of application No. 09/563,899, filed on May 3, 2000, now abandoned.

(60) Provisional application No. 60/132,360, filed on May 4, 1999.

(51) Int. Cl.
*C12N 15/00* (2006.01)
(52) U.S. Cl. .............................. 435/455; 435/5; 435/6; 435/7.72; 435/7.9; 435/7.91; 435/8; 435/21; 435/23; 435/69.1; 435/456
(58) Field of Classification Search .................... 435/5, 435/6, 7.72, 7.9, 7.91, 8, 21, 23, 69.1, 455, 435/456
See application file for complete search history.

(56) References Cited

U.S. PATENT DOCUMENTS

| 5,861,267 A | 1/1999 | Su |
| 6,280,940 B1 * | 8/2001 | Potts et al. ..................... 435/6 |

FOREIGN PATENT DOCUMENTS

| WO | WO98/00548 A1 | 1/1998 |
| WO | WO 00/08469 A1 | 2/2000 |
| WO | WO 00/12727 A1 | 3/2000 |

OTHER PUBLICATIONS

Hirowatari et al. (Analytical Biochemistry, 1995, vol. 225, pp. 113-120).*
Bowie et al (Science, 1990, 257:1306-1310).*
Burgess et al (J. of Cell Bio. 111:2129-2138, 1990).*
Bork (Genome Research, 2000,10:398-400).*
Lohman, V., et al, Replication of Subgenomic Hepatitis C Virus RNAs in a Hepatoma Cell Line, 1999, Science, 285:110-113.
Kim, J.-E., et al, Subcellular localization of hepatitis C viral proteins in mammalian cells, 1999, Arch. Virol. 144: 329-343.
Hirowatari, Y., et al, A Novel Method for Analysis of Viral Proteinase Activity Encoded by Hepatitis C Virus in Cultured Cells, 1995 Analytical Biochem. 225: 113-120.
Overton, H., et al, Recombinant baculovirus-expressed NS3 proteinase of hepatitis C virus shows activity in cell-based and in vitro assays, 1995, J. Gen. Virol. 76: 3009-3019.
Song, O-K, et al, Development of an in vivo Assay System Suitable for Screening Inhibitors of Hepatitis C Viral Protease, Mol. Cells, 1996, 6 (2): 183-189.
Cho, Y-G, et al, Construction of hepatitis C-SIN virus recombinants with replicative dependency on hepatitis C virus serine protease activity, 1997, J. Virol. Methods, 65: pp. 201-207.
Cho, Y-G., et al, In vivo assay for hepatitis C viral serine protease activity using a secreted protein, 02 1998, .f Virol. Methods, 72: 109-115.

* cited by examiner

*Primary Examiner*—Robert A. Zeman
(74) *Attorney, Agent, or Firm*—Michael P. Morris; Mary-Ellen M. Devlin; Philip I. Datlow

(57) ABSTRACT

The present invention concerns the development of a cell-based assay system having improved sensitivity to HCV NS3 protease activity when compared to known assays, which is useful for screening test compounds capable of modulating (particularly inhibiting) HCV NS3 protease activity. This system provides a first construct comprising a transactivator domain joined downstream of the NS3–5 domains of HCV under the control of a non-cytopathic viral promoter system. A second construct is also provided that comprises a reporter gene under the control of an operator sensitive to the binding of the transactivator. The NS3–5 domains encodes the NS3 polyprotein which comprises: the NS3 protease, followed by the NS4A co-factor, the NS4B and NS5A proteins (including any derivative, variant or fragment thereof), terminated by the NS5B protein (including any derivative, variant or fragment thereof) sufficient to constitute a NS5A/5B cleavage site. The transactivator, when expressed and released from the polyprotein initiates transcription and expression of the reporter gene that is measurable.

15 Claims, 17 Drawing Sheets

FIGURE 1
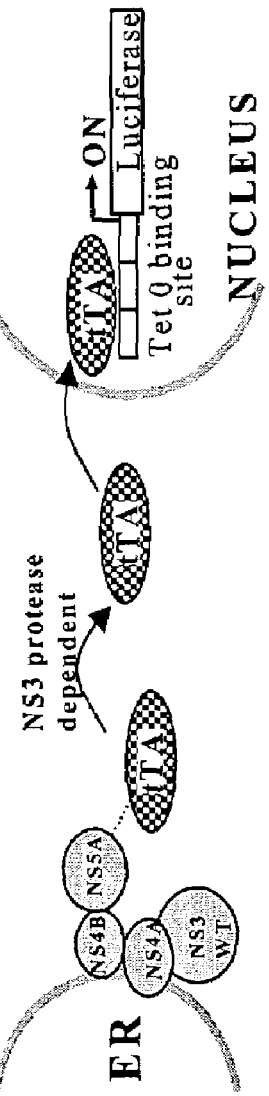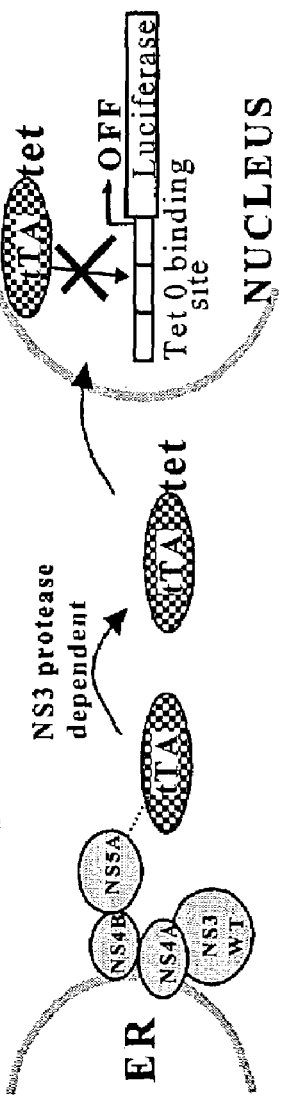

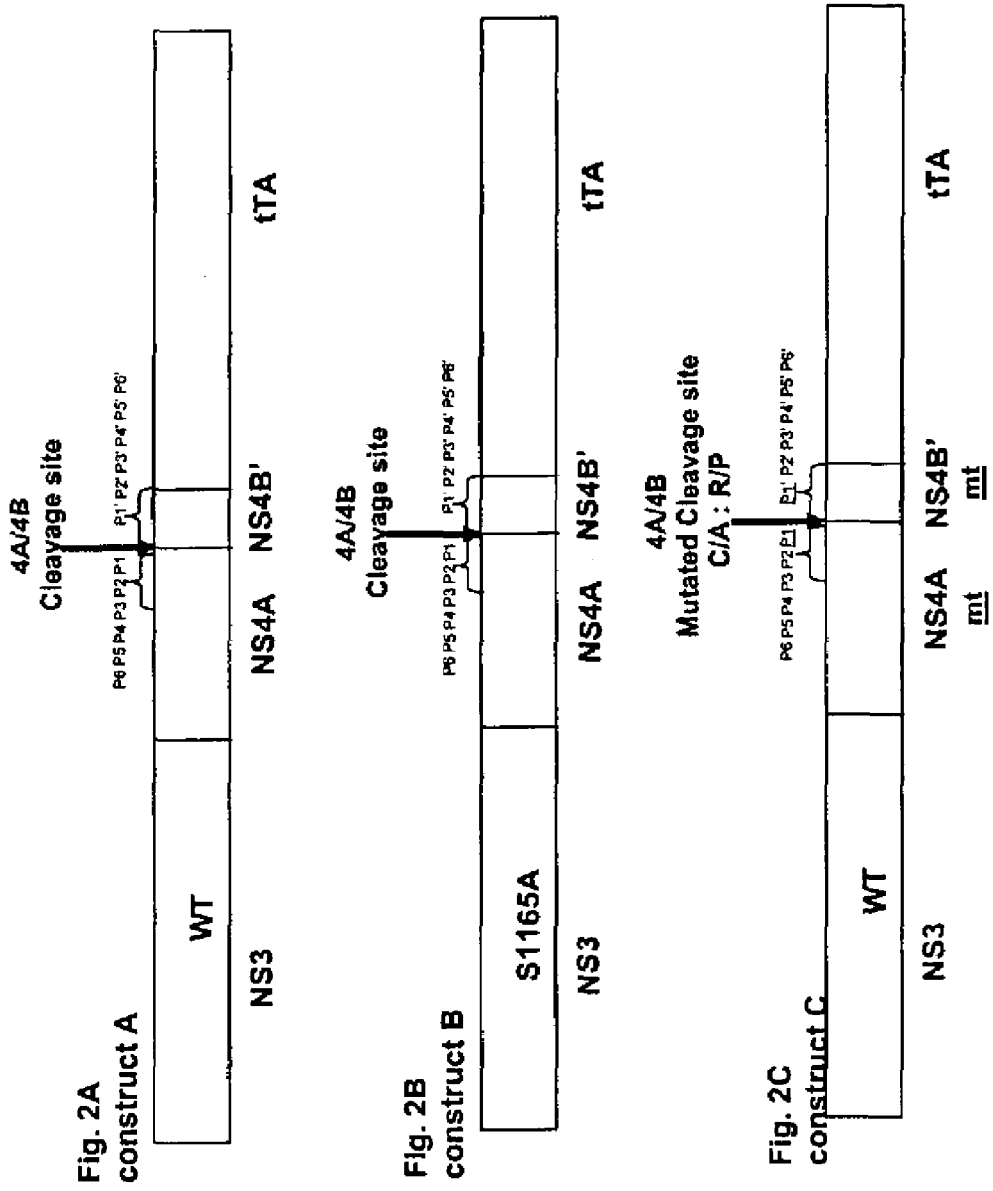

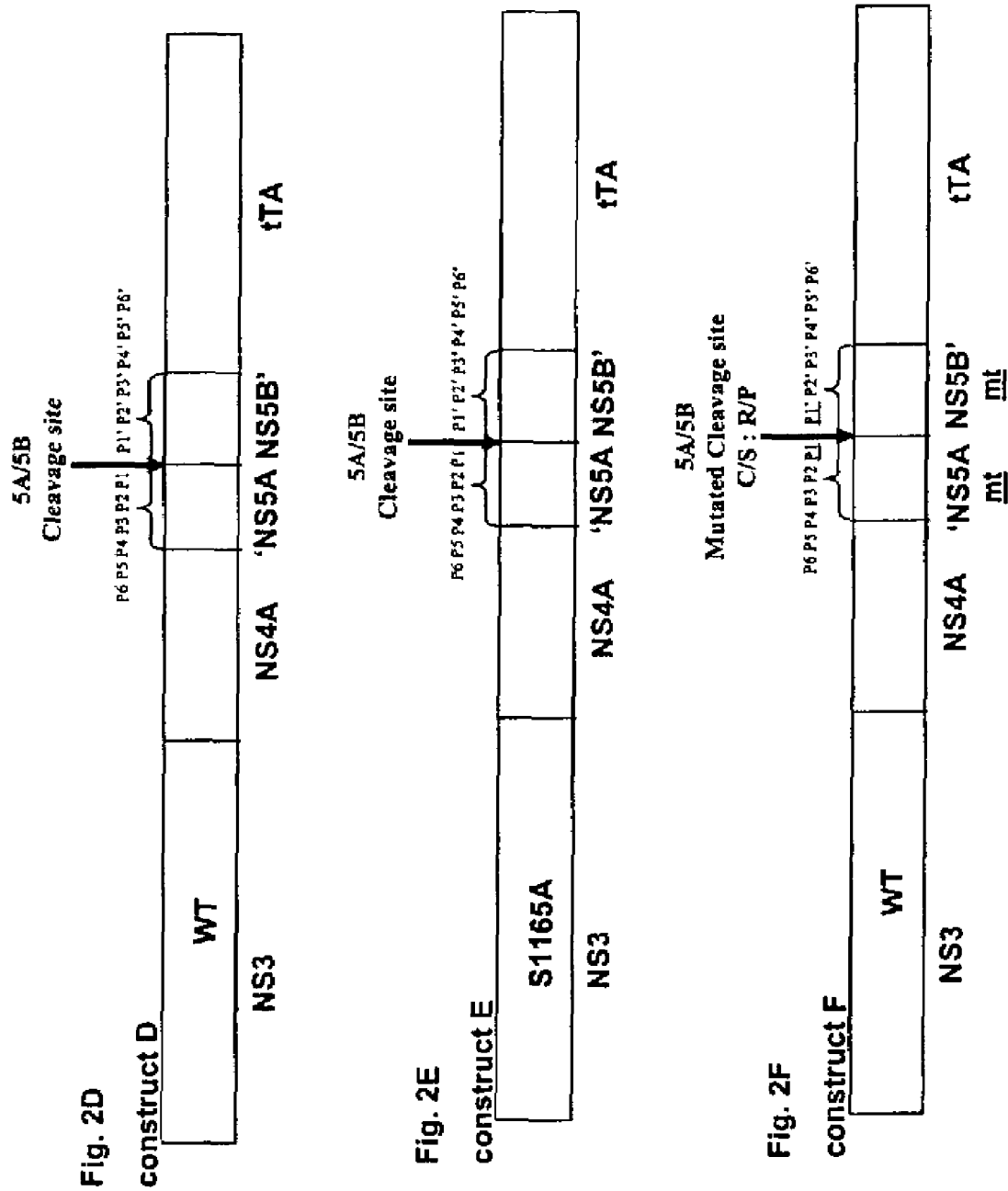

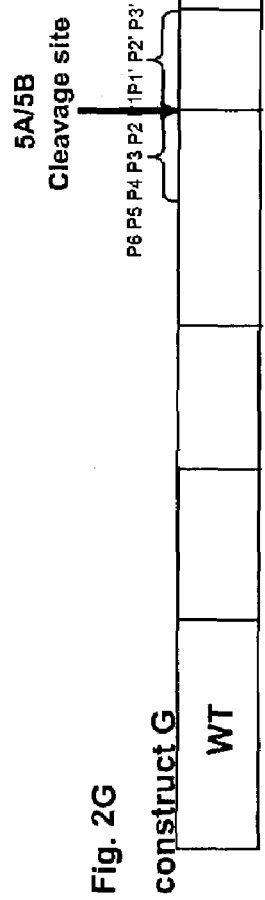
Fig. 2G construct G
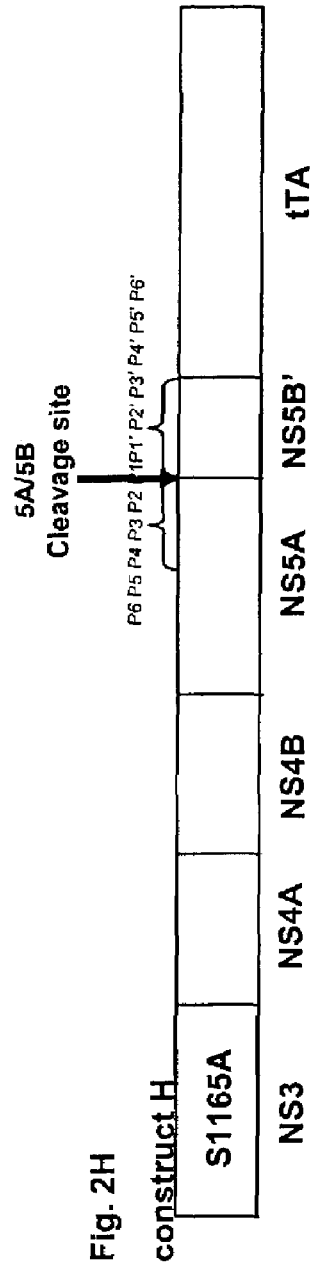
Fig. 2H construct H
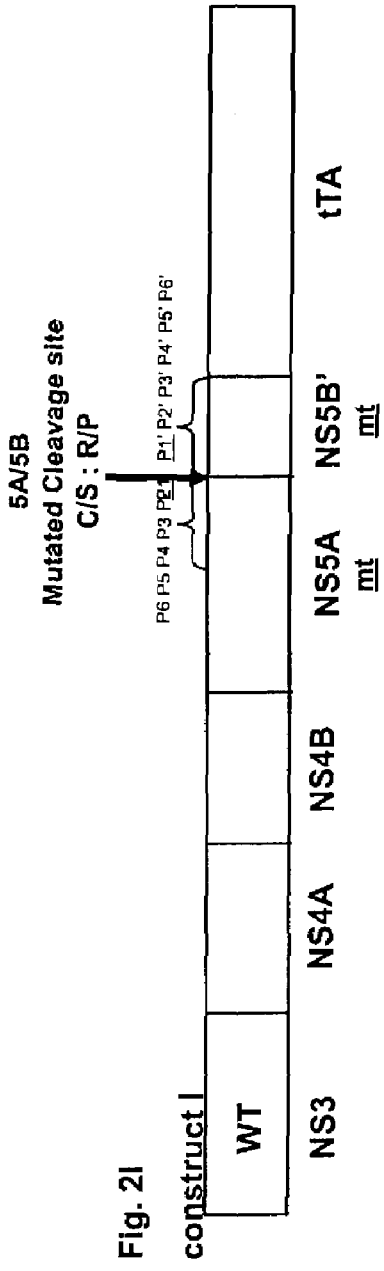
Fig. 2I construct I

FIGURE 3
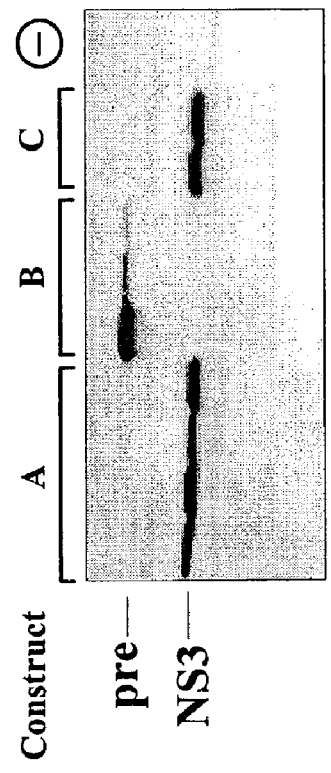
Fig. 3A
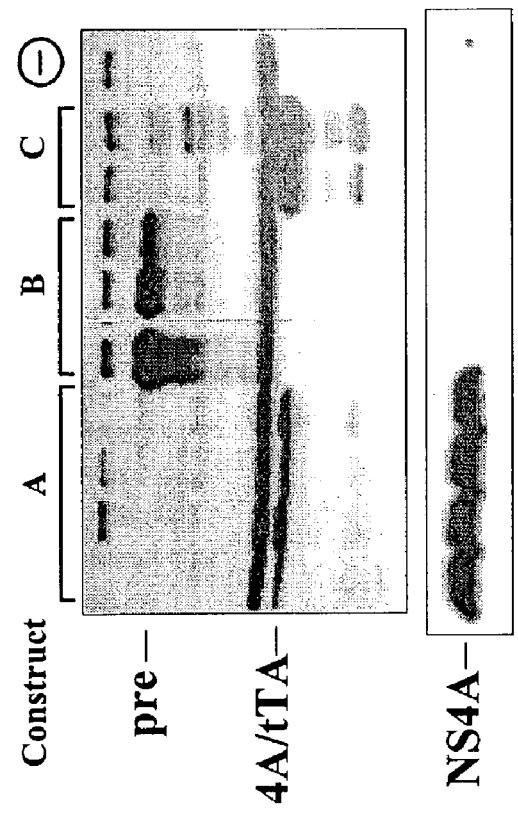
Fig. 3B

FIGURE 5
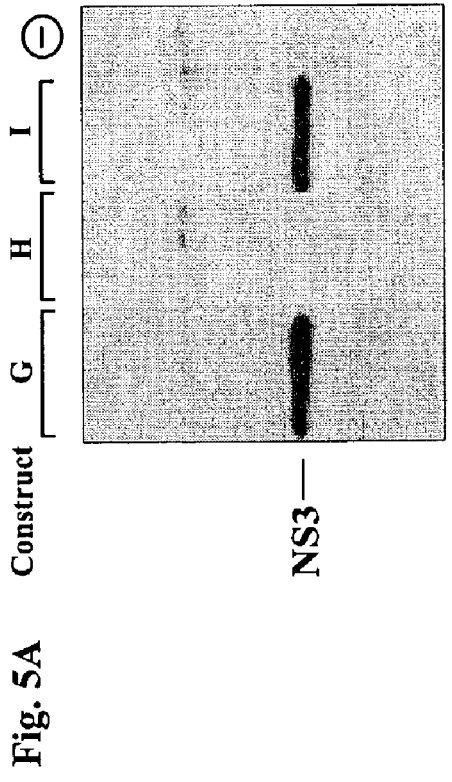
Fig. 5A
Fig. 5C
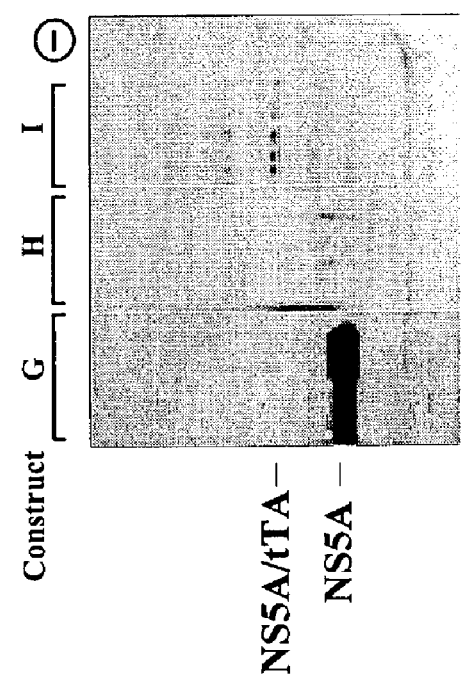
Fig. 5B

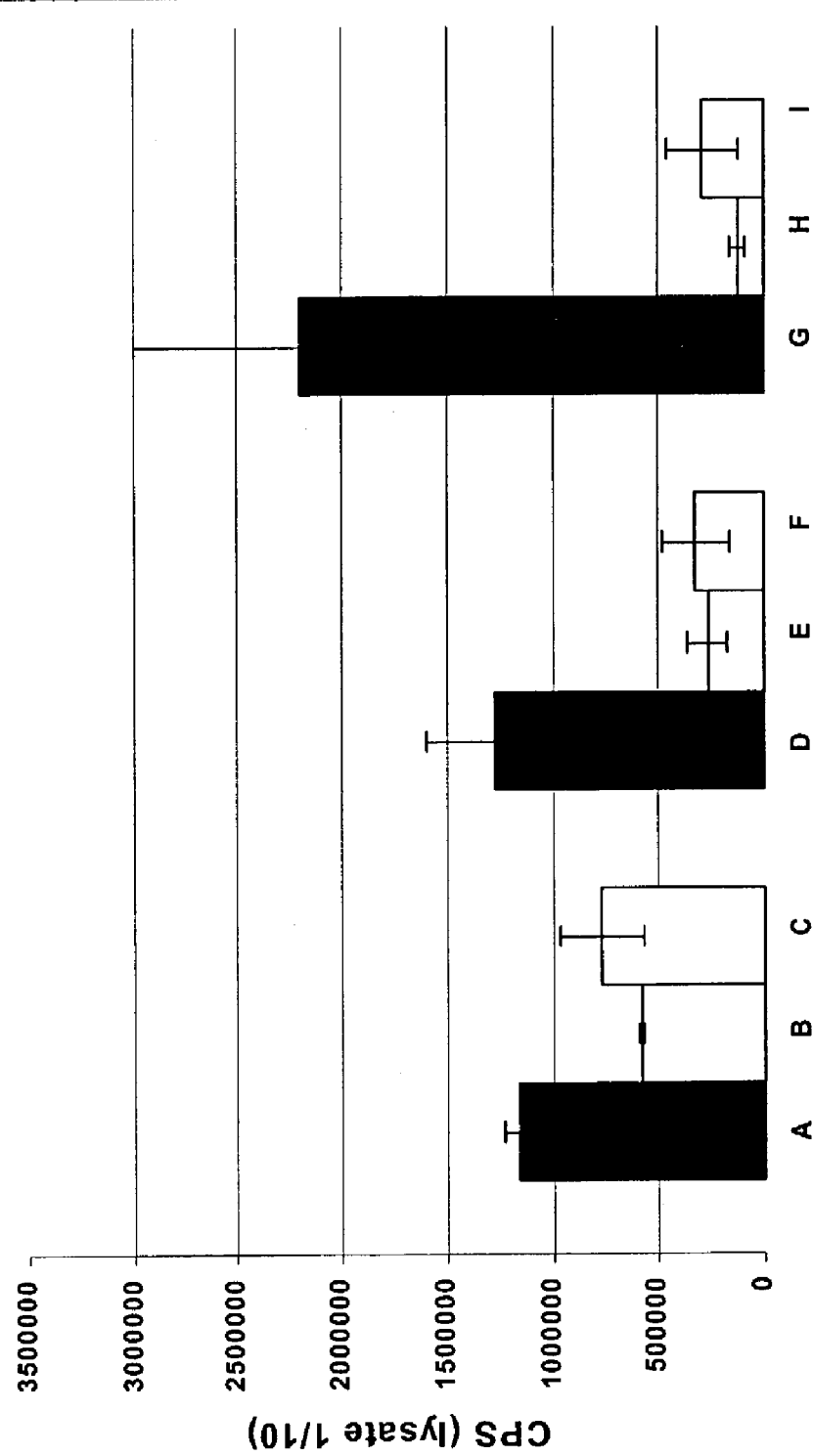

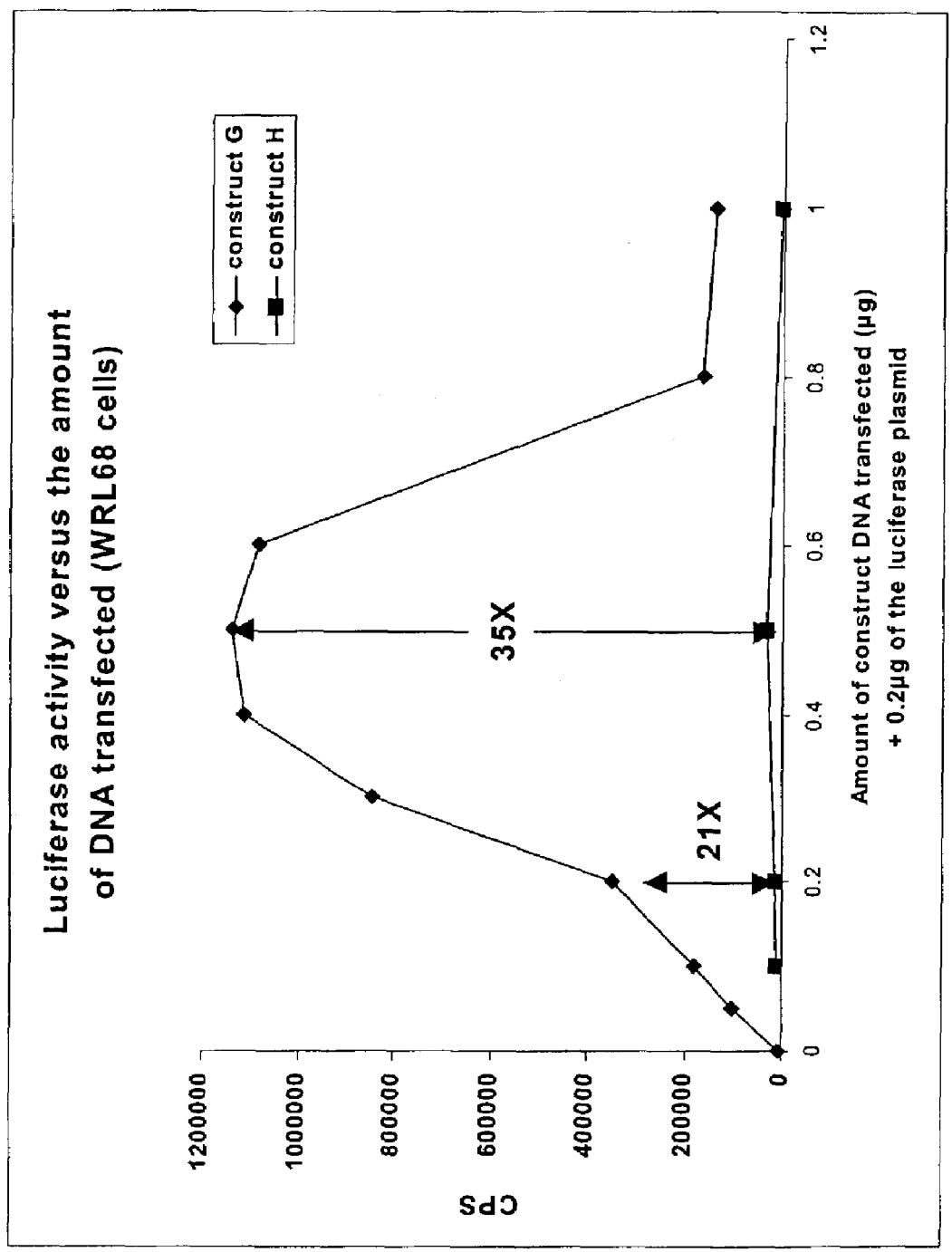

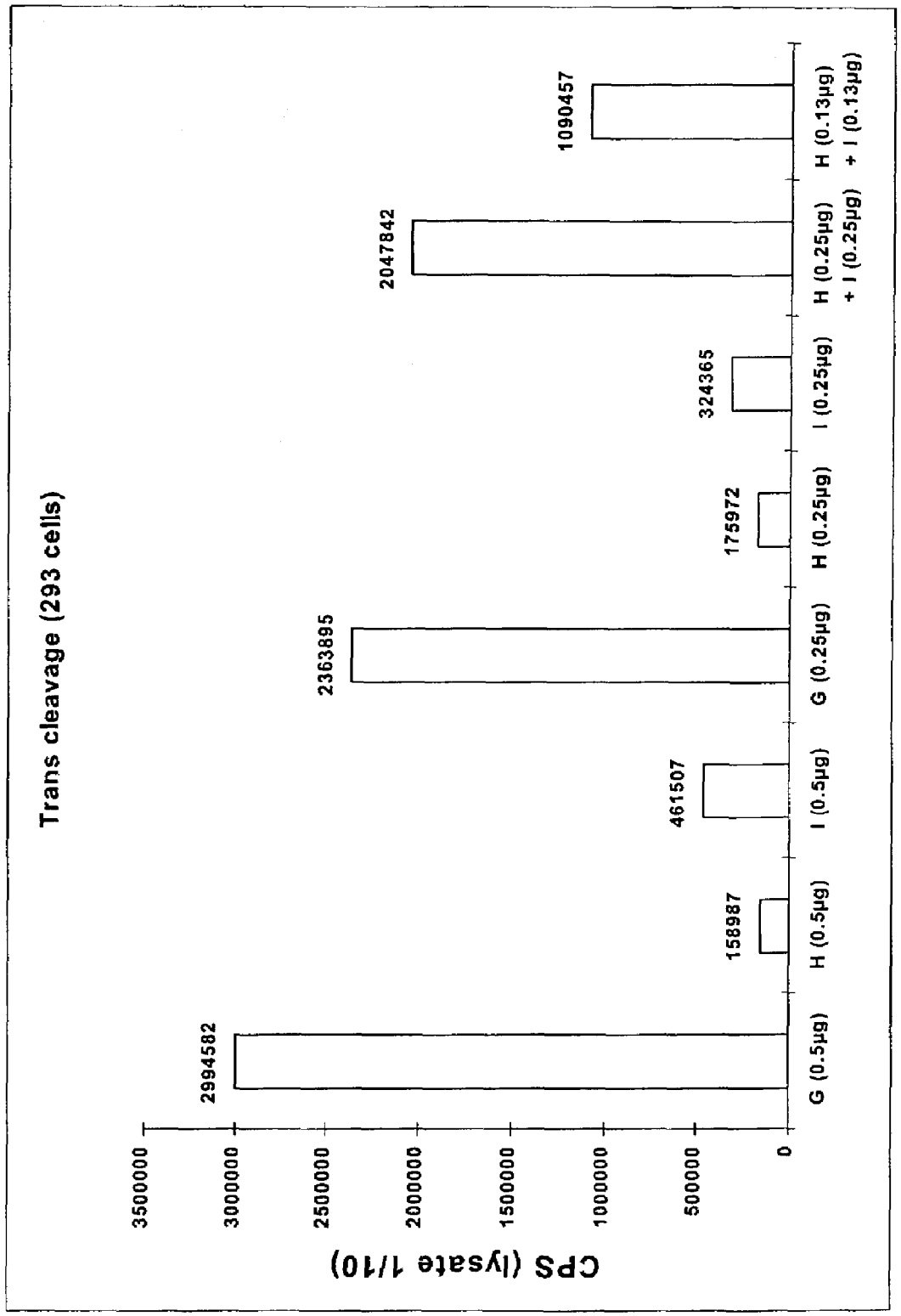

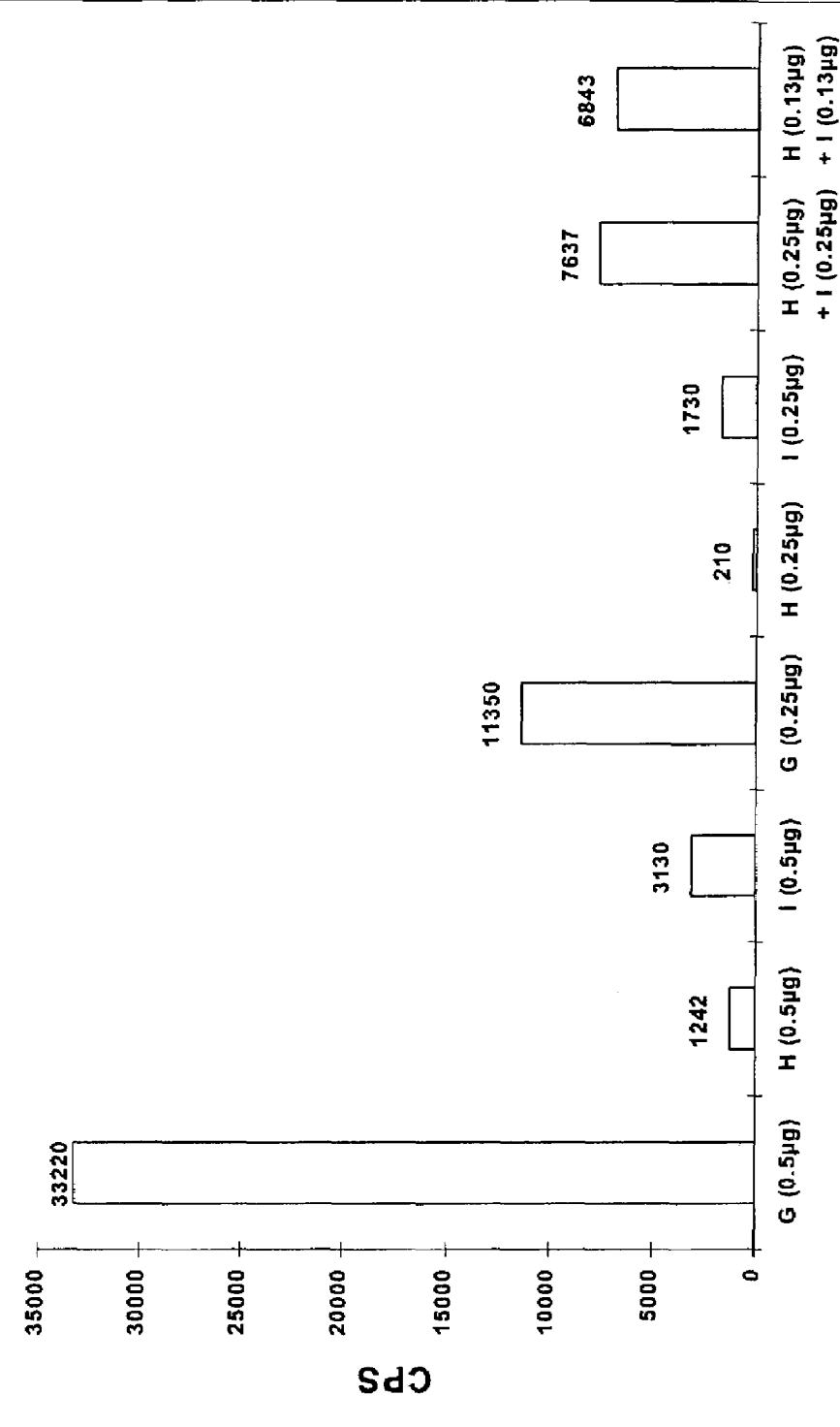

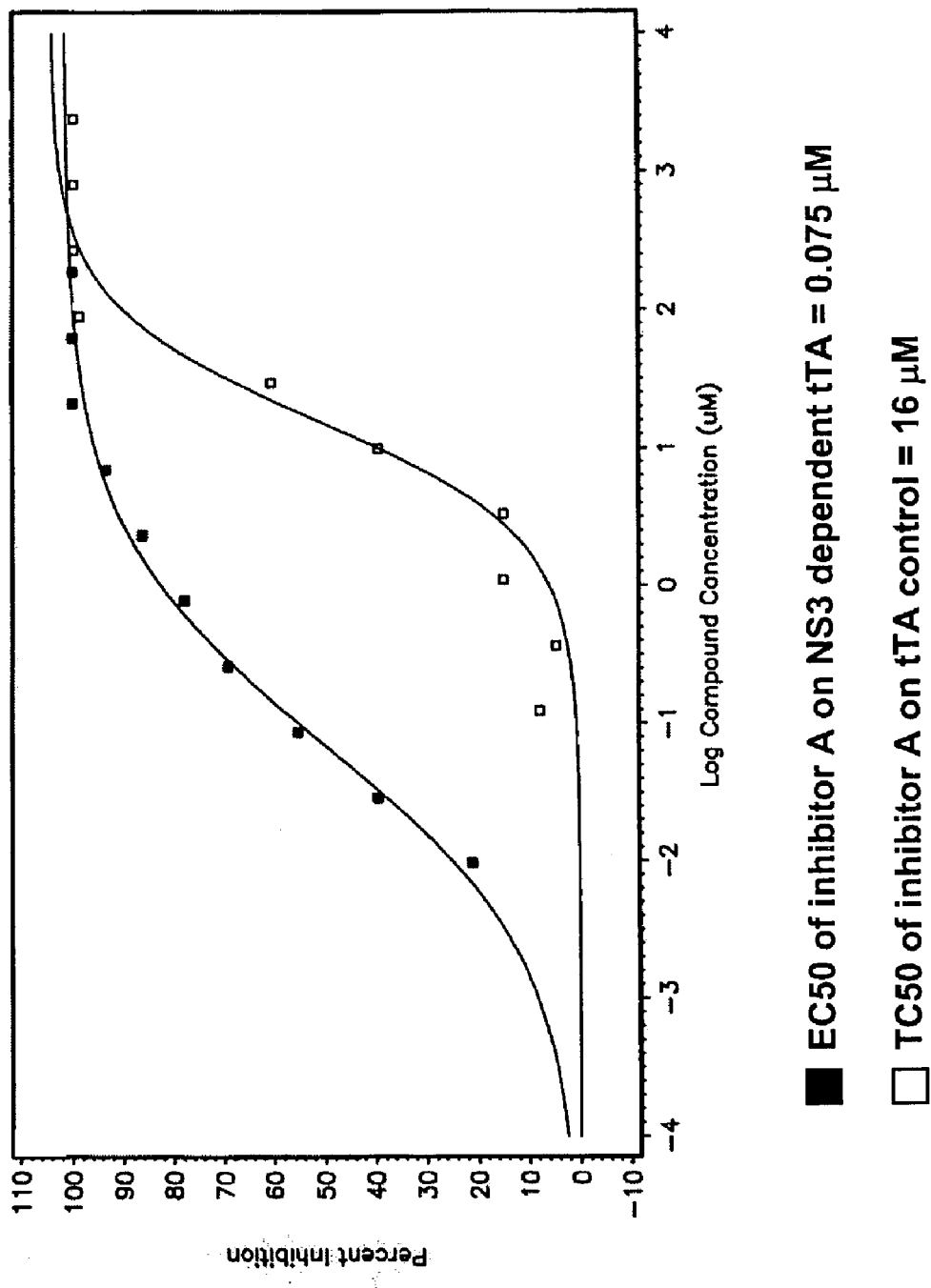

SEQUENCE LISTING

<160> NUMBER OF SEQ ID NOS: 9

<210> SEQ ID NO 1
<211> LENGTH: 5211
<212> TYPE: DNA
<213> ORGANISM: Artificial Sequence
<220> FEATURE:
<223> OTHER INFORMATION: Description of Artificial Sequence: partial cDNA sequence of HCV (NS3-5B') fused to tTA transactivator

<400> SEQUENCE: 1

| | | | | | | |
|---|---|---|---|---|---|---|
| atgtctagcg | cgcccatcac | ggcctactcc | aacagacac | ggggcctact | tggttgcatc | 60 |
| atcaccagcc | tcacaggccg | ggacaagaac | caggtcgagg | gggaggttca | agtggtttcc | 120 |
| accgcaacac | aatctttcct | ggcgacctgc | gtcaacggcg | tgtgttggac | tgtcttccat | 180 |
| ggcgccggct | caaagacctt | ggccggcccc | aaaggcccga | tcacccagat | gtacactaat | 240 |
| gtggaccagg | acctcgtcgg | ctggcaggcg | cccctgggg | cgcgctccat | gacaccatgc | 300 |
| acctgcggca | gctcggacct | ctatttggtc | acgagacatg | ccgacgtcat | tccggtgcgc | 360 |
| cggcggggca | cagtagggg | gagcctgctc | tcccccaggc | ctgtctccta | cttgaagggc | 420 |
| tcttcggggtg | gcccactgct | ctgcccttcg | gggcacgctg | tgggcatctt | ccgggctgct | 480 |
| gtgtgcaccc | gggggttgc | aaaagcggtg | gacttcatac | ctgttgagtc | tatggaaact | 540 |
| actatgcggt | ctccggtctt | cacagacaac | tcatcccccc | cagccgtacc | gcagacattc | 600 |
| caagtggccc | atctacacgc | tcctactggc | agcggcaaga | gcactaaagt | gccggctgct | 660 |
| tatgcagccc | aagggtacaa | ggtacttgtc | ttgaacccgt | ccgttgccgc | cacccttaggt | 720 |
| tttgggggcgt | atatgtcaaa | ggcacgtggc | accgaccctaa | acatcagaac | tggggtaagg | 780 |
| accatcacca | caggcgcccc | catcacgtac | tccacctatg | gcaagttcct | tgccgacggt | 840 |
| ggttgctctg | gggcgctta | tgacatcata | atgtgtgacg | agtgccactc | aactgactcg | 900 |
| actaccatct | tgggcatcgg | cacagtcctg | gaccaagcgg | agacggctgg | agcgcggctt | 960 |
| gtcgtgctcg | ccaccgctac | gcctccggga | tcggtcaccg | tgccacaccc | caatatcgag | 1020 |
| gaggtggccc | tgtccaacac | tggagagatc | cccttctatg | gcaaagccat | ccccatcgag | 1080 |
| gtcatcaagg | ggggaaggca | tctcattttc | tgccattcca | aaaagaagtg | tgatgagctc | 1140 |
| gccgcaaagc | tgtcgggcct | cggactcaac | gccgtagcgt | attaccgggg | ccttgatgtg | 1200 |
| tccgtcatac | cgaccagcgg | agacgtcgtt | gttgtggcaa | cagacgcctt | aatgaccggc | 1260 |
| tttaccggcg | actttgattc | agtgatcgac | tgcaatacgt | gtgttaccca | gacagtcgat | 1320 |
| ttcagcttgg | accccacctt | caccattgag | acgacgaccg | tgcctcaaga | cgcggtgtcg | 1380 |
| cgctcgcagc | ggcggggtag | gactggcagg | ggtaggagag | gcatctacag | gtttgtgact | 1440 |
| ccaggagaac | ggccttcggg | catgttcgat | tcctcggtcc | tatgtgagtg | ctatgacgcg | 1500 |
| ggctgtgctt | ggtatgagct | cacgcccgct | gagaccacgt | cagattgcg | ggcttaccta | 1560 |
| aacacaccag | ggttgcccgt | ctgtcaggac | catctggagt | tctggagggg | cgtcttcacg | 1620 |
| ggcctcaccc | acatagatgc | ccacttcttg | tcccagacta | agcaggcagg | agacaacttc | 1680 |
| ccctacctgg | tagcgtacca | agccacagtg | tgcgctagag | ctcaggcccc | acctccatcg | 1740 |
| tgggatcaaa | tgtggaagtg | tctcatacgg | ctaaaaccta | cgctgcacgg | gccaacaccc | 1800 |
| ctgctgtata | ggctaggagc | cgtccaaaat | gagatcaccc | tcacacaccc | cgtgaccaaa | 1860 |
| tacatcatga | catgcatgtc | ggccgacctg | gaggtcgtca | ctagcacctg | ggtgctagta | 1920 |
| ggcgggggtcc | ttgcagcttt | ggccgcatat | tgcctgacaa | caggcagtgt | ggtcattgtg | 1980 |
| ggtaggatca | tcttatccgg | gaggccggca | gtggttcccg | acaggggaagt | cctctaccgg | 2040 |
| gagttcgatg | aaatggaaga | gtgcgcctca | cacctccctt | acatcgaaca | gggaatgcag | 2100 |
| cttgccgagc | aattcaagca | gaaggcgctc | gggttgctgc | agacagccac | caagcaagcg | 2160 |
| gaggctgctg | ctcccgtggt | ggagtccaag | tggcgagccc | tcgagacctt | ctgggcgaag | 2220 |

```
cacatgtgga acttcatcag cgggatacag tacttagcag gcttgtccac tctgcctgga    2280
aaccccgcga tagcatcatt gatggcattt acagcctcta tcaccagccc gctcactacc    2340
caaaataccc tcctgtttaa tatcttggga ggatgggtgg ctgcccaact cgccgccccc    2400
ggtgctgctt cggctttcgt gggcgccggc atcgtcggtg cggctgttgg cagcataggc    2460
cttgggaagg tgctcgtgga cattctggcg ggctatgggg caggggtggc tggcgcactc    2520
gtggctttta agatcatgag cggcgaggtg ccctccaccg aggacctggt taatttactc    2580
cctgccattc tttctcctgg cgccctggtt gtcggggtcg tgtgcgcagc aatactgcgt    2640
cggcacgtgg gcccgggggga gggggctgtg cagtggatga accggctgat agcgttcgct    2700
tcgcggggca accacgtttc ccccacgcac tatgtgcctg agagcgacgc cgcagcgcgt    2760
gttacccaga tcctctccgg ccttaccatc actcagctgc tgaagaggct tcatcagtgg    2820
atcaatgagg actgctccac gccatgctcc ggttcgtggc taagggatgt ttgggactgg    2880
atatgcacgg tgttggctga tttcaagacc tggctccagt ccaagctcct accgcggtta    2940
ccgggagtcc ccttcctctc atgccaacga gggtataagg gagtctggcg gggggatggt    3000
atcatgcaca ccacctgccc ctgtggagca caaatcaccg gacatgtcaa aaacggttcc    3060
atgcggatcg tcgggcctag gacctgcagc aacacgtggc acggaacatt ccccatcaac    3120
gcgtacacca cggcccctg cacaccctcc ccggcgccga attaccaccag ggcgctatgg    3180 cgggtagctg ctgaggagta cgtggaggtc acgcgggtgg gggatttcca ctacgtgacg    3240
ggcatgacca ccgacaacgt aaagtgccca tgccaggttc cggcccccga gttcttcacg    3300
gaagttgatg gggtacggtt gcacaggtac gctccggtgt gcagacctct cctacgggag    3360
gaggtcgtat tccaggtcgg gctcaaccaa tacctggttg gatcacagct cccatgcgag    3420
cccgaaccgg atgtggcagt gctcacttcc atgctcaccg acccctccca cattacagca    3480
gagacggcta agcgtaggct ggccaggggg tcaccccccct ccttggccag ctcttctgcc    3540
agccagttat ctgcgccttc cttgaaggcg acatgcacta ctcatcatga ctccccggac    3600
gccgacctca tcgaggccaa cctcctgtgg cggcaggaga tgggcgggaa catcacccgc    3660
gtggagtcag agaataaggt agtaattctg gactcttttcg attcgcttcg agcggaggag    3720
gatgagaggg aaatatccgt tgaggcggaa atcctgcgga gatccaagaa gttcccccca    3780
gcgatgccca tatgggcacg cccggattac aaccctccac tgctagagtc ctggaaggac    3840
ccggactacg tccctccggt ggtacacggg tgcccattgc cacctaccaa ggccctccca    3900
ataccacctc cacggaggaa aaagacggtt gtcctaacag agtccaccgt ctcttctgcc    3960
ttggcagagc ttgcttctaa gaccttggc agctctggat cgtcggccgt cgacagcggc    4020
acggcgaccc tcctcccga ccaggcctcc gacgacggcg acaaagaatc cgacgttgag    4080
tcgtactcct ccatgccccc tcttgagggg gagccggggg accccgatct agcgacggg    4140 tcttggtcta ccgtgagtga ggaggccggt gaggacgtcg tctgctgctc gatgtcctac    4200
acatggtcta gattagataa aagtaaagtg attaacagcg cattagagct gcttaatgac    4260
gtcggaatcg aaggtttaac aacccgtaaa ctcgcccaga agctaggtgt agagcagcct    4320
acattgtatt ggcatgtaaa aaataagcgg gctttgctcg acgccttagc cattgagatg    4380
ttagataggc accatactca cttttgcccct ttagaagggg aaagctggca agatttttta    4440
cgtaataacg ctaaaagttt tagatgtgct ttactaagtc atcgcgatgg agcaaaagta    4500
catttaggta cacggcctac agaaaaacag tatgaaactc tcgaaaatca attagccttt    4560
ttatgccaac aaggttttttc actagagaat gcattatatg cactcagcgc tgtggggcat    4620
```

-continued

```
tttactttag gttgcgtatt ggaagatcaa gagcatcaag tcgctaaaga agaaagggaa    4680
acacctacta ctgatagtat gccgccatta ttacgacaag ctatcgaatt atttgatcac    4740
caaggtgcag agccagcctt cttattcggc cttgaattga tcatatgcgg attagaaaaa    4800
caacttaaat gtgaaagtgg gtccgcgtac agccgcgcgc gtacgaaaaa caattacggg    4860
tctaccatcg agggcctgct cgatctcccg gacgacgacg ccccgaaga ggcggggctg     4920 gcggctccgc gcctgtcctt tctccccgcg ggacacacgc gcagactgtc gacggccccc    4980
ccgaccgatg tcagcctggg ggacgagctc cacttagacg gcgaggacgt ggcgatggcg    5040
catgccgacg cgctagacga tttcgatctg gacatgttgg gggacgggga ttccccgggt    5100
ccgggattta ccccccacga ctccgccccc tacggcgctc tggatatggc cgacttcgag    5160
tttgagcaga tgtttaccga tgcccttgga attgacgagt acggtgggta g             5211
```

<210> SEQ ID NO 2
<211> LENGTH: 1736
<212> TYPE: PRT
<213> ORGANISM: Artificial Sequence
<220> FEATURE:
<223> OTHER INFORMATION: Description of Artificial Sequence: partial HCV
   polyprotein region (NS3-5B') fused to tTA
   transactivator

<400> SEQUENCE: 2

```
Met Ser Ser Ala Pro Ile Thr Ala Tyr Ser Gln Gln Thr Arg Gly Leu
 1               5                  10                  15

Leu Gly Cys Ile Ile Thr Ser Leu Thr Gly Arg Asp Lys Asn Gln Val
            20                  25                  30

Glu Gly Glu Val Gln Val Val Ser Thr Ala Thr Gln Ser Phe Leu Ala
        35                  40                  45

Thr Cys Val Asn Gly Val Cys Trp Thr Val Phe His Gly Ala Gly Ser
    50                  55                  60

Lys Thr Leu Ala Gly Pro Lys Gly Pro Ile Thr Gln Met Tyr Thr Asn
65                  70                  75                  80

Val Asp Gln Asp Leu Val Gly Trp Gln Ala Pro Pro Gly Ala Arg Ser
                85                  90                  95

Met Thr Pro Cys Thr Cys Gly Ser Ser Asp Leu Tyr Leu Val Thr Arg
            100                 105                 110

His Ala Asp Val Ile Pro Val Arg Arg Arg Gly Asp Ser Arg Gly Ser
        115                 120                 125

Leu Leu Ser Pro Arg Pro Val Ser Tyr Leu Lys Gly Ser Ser Gly Gly
    130                 135                 140

Pro Leu Leu Cys Pro Ser Gly His Ala Val Gly Ile Phe Arg Ala Ala
145                 150                 155                 160

Val Cys Thr Arg Gly Val Ala Lys Ala Val Asp Phe Ile Pro Val Glu
                165                 170                 175

Ser Met Glu Thr Thr Met Arg Ser Pro Val Phe Thr Asp Asn Ser Ser
            180                 185                 190

Pro Pro Ala Val Pro Gln Thr Phe Gln Val Ala His Leu His Ala Pro
        195                 200                 205

Thr Gly Ser Gly Lys Ser Thr Lys Val Pro Ala Ala Tyr Ala Ala Gln
    210                 215                 220

Gly Tyr Lys Val Leu Val Leu Asn Pro Ser Val Ala Ala Thr Leu Gly
225                 230                 235                 240

Phe Gly Ala Tyr Met Ser Lys Ala Arg Gly Thr Asp Pro Asn Ile Arg
                245                 250                 255
```

```
Thr Gly Val Arg Thr Ile Thr Thr Gly Ala Pro Ile Thr Tyr Ser Thr
            260                 265                 270

Tyr Gly Lys Phe Leu Ala Asp Gly Gly Cys Ser Gly Gly Ala Tyr Asp
            275                 280                 285

Ile Ile Met Cys Asp Glu Cys His Ser Thr Asp Ser Thr Thr Ile Leu
            290                 295                 300

Gly Ile Gly Thr Val Leu Asp Gln Ala Glu Thr Ala Gly Ala Arg Leu
305                 310                 315                 320

Val Val Leu Ala Thr Ala Thr Pro Pro Gly Ser Val Thr Val Pro His
            325                 330                 335

Pro Asn Ile Glu Glu Val Ala Leu Ser Asn Thr Gly Glu Ile Pro Phe
            340                 345                 350

Tyr Gly Lys Ala Ile Pro Ile Glu Val Ile Lys Gly Gly Arg His Leu
            355                 360                 365

Ile Phe Cys His Ser Lys Lys Lys Cys Asp Glu Leu Ala Ala Lys Leu
            370                 375                 380

Ser Gly Leu Gly Leu Asn Ala Val Ala Tyr Tyr Arg Gly Leu Asp Val
385                 390                 395                 400

Ser Val Ile Pro Thr Ser Gly Asp Val Val Val Val Ala Thr Asp Ala
            405                 410                 415

Leu Met Thr Gly Phe Thr Gly Asp Phe Asp Ser Val Ile Asp Cys Asn
            420                 425                 430

Thr Cys Val Thr Gln Thr Val Asp Phe Ser Leu Asp Pro Thr Phe Thr
            435                 440                 445

Ile Glu Thr Thr Thr Val Pro Gln Asp Ala Val Ser Arg Ser Gln Arg
450                 455                 460

Arg Gly Arg Thr Gly Arg Gly Arg Arg Gly Ile Tyr Arg Phe Val Thr
465                 470                 475                 480

Pro Gly Glu Arg Pro Ser Gly Met Phe Asp Ser Ser Val Leu Cys Glu
            485                 490                 495

Cys Tyr Asp Ala Gly Cys Ala Trp Tyr Glu Leu Thr Pro Ala Glu Thr
            500                 505                 510

Thr Val Arg Leu Arg Ala Tyr Leu Asn Thr Pro Gly Leu Pro Val Cys
            515                 520                 525

Gln Asp His Leu Glu Phe Trp Glu Gly Val Phe Thr Gly Leu Thr His
            530                 535                 540

Ile Asp Ala His Phe Leu Ser Gln Thr Lys Gln Ala Gly Asp Asn Phe
545                 550                 555                 560

Pro Tyr Leu Val Ala Tyr Gln Ala Thr Val Cys Ala Arg Ala Gln Ala
            565                 570                 575

Pro Pro Pro Ser Trp Asp Gln Met Trp Lys Cys Leu Ile Arg Leu Lys
            580                 585                 590

Pro Thr Leu His Gly Pro Thr Pro Leu Leu Tyr Arg Leu Gly Ala Val
            595                 600                 605

Gln Asn Glu Ile Thr Leu Thr His Pro Val Thr Lys Tyr Ile Met Thr
610                 615                 620

Cys Met Ser Ala Asp Leu Glu Val Val Thr Ser Thr Trp Val Leu Val
625                 630                 635                 640

Gly Gly Val Leu Ala Ala Leu Ala Ala Tyr Cys Leu Thr Thr Gly Ser
            645                 650                 655

Val Val Ile Val Gly Arg Ile Ile Leu Ser Gly Arg Pro Ala Val Val
            660                 665                 670
```

```
Pro Asp Arg Glu Val Leu Tyr Arg Glu Phe Asp Glu Met Glu Glu Cys
        675                 680                 685

Ala Ser His Leu Pro Tyr Ile Glu Gln Gly Met Gln Leu Ala Glu Gln
    690                 695                 700

Phe Lys Gln Lys Ala Leu Gly Leu Leu Gln Thr Ala Thr Lys Gln Ala
705                 710                 715                 720

Glu Ala Ala Pro Val Val Glu Ser Lys Trp Arg Ala Leu Glu Thr
                725                 730                 735

Phe Trp Ala Lys His Met Trp Asn Phe Ile Ser Gly Ile Gln Tyr Leu
                740                 745                 750

Ala Gly Leu Ser Thr Leu Pro Gly Asn Pro Ala Ile Ala Ser Leu Met
            755                 760                 765

Ala Phe Thr Ala Ser Ile Thr Ser Pro Leu Thr Thr Gln Asn Thr Leu
    770                 775                 780

Leu Phe Asn Ile Leu Gly Gly Trp Val Ala Ala Gln Leu Ala Ala Pro
785                 790                 795                 800

Gly Ala Ala Ser Ala Phe Val Gly Ala Gly Ile Val Gly Ala Ala Val
                805                 810                 815

Gly Ser Ile Gly Leu Gly Lys Val Leu Val Asp Ile Leu Ala Gly Tyr
            820                 825                 830

Gly Ala Gly Val Ala Gly Ala Leu Val Ala Phe Lys Ile Met Ser Gly
    835                 840                 845

Glu Val Pro Ser Thr Glu Asp Leu Val Asn Leu Leu Pro Ala Ile Leu
850                 855                 860

Ser Pro Gly Ala Leu Val Val Gly Val Val Cys Ala Ala Ile Leu Arg
865                 870                 875                 880

Arg His Val Gly Pro Gly Glu Gly Ala Val Gln Trp Met Asn Arg Leu
                885                 890                 895

Ile Ala Phe Ala Ser Arg Gly Asn His Val Ser Pro Thr His Tyr Val
            900                 905                 910

Pro Glu Ser Asp Ala Ala Ala Arg Val Thr Gln Ile Leu Ser Gly Leu
    915                 920                 925

Thr Ile Thr Gln Leu Leu Lys Arg Leu His Gln Trp Ile Asn Glu Asp
    930                 935                 940

Cys Ser Thr Pro Cys Ser Gly Ser Trp Leu Arg Asp Val Trp Asp Trp
945                 950                 955                 960

Ile Cys Thr Val Leu Ala Asp Phe Lys Thr Trp Leu Gln Ser Lys Leu
                965                 970                 975

Leu Pro Arg Leu Pro Gly Val Pro Phe Leu Ser Cys Gln Arg Gly Tyr
            980                 985                 990

Lys Gly Val Trp Arg Gly Asp Gly Ile Met His Thr Thr Cys Pro Cys
    995                 1000                1005

Gly Ala Gln Ile Thr Gly His Val Lys Asn Gly Ser Met Arg Ile Val
    1010                1015                1020

Gly Pro Arg Thr Cys Ser Asn Thr Trp His Gly Thr Phe Pro Ile Asn
1025                1030                1035                1040

Ala Tyr Thr Thr Gly Pro Cys Thr Pro Ser Pro Ala Pro Asn Tyr Thr
                1045                1050                1055

Arg Ala Leu Trp Arg Val Ala Ala Glu Glu Tyr Val Glu Val Thr Arg
            1060                1065                1070

Val Gly Asp Phe His Tyr Val Thr Gly Met Thr Thr Asp Asn Val Lys
    1075                1080                1085
```

-continued

```
Cys Pro Cys Gln Val Pro Ala Pro Glu Phe Phe Thr Glu Val Asp Gly
    1090                1095                1100
Val Arg Leu His Arg Tyr Ala Pro Val Cys Arg Pro Leu Leu Arg Glu
1105                1110                1115                1120
Glu Val Val Phe Gln Val Gly Leu Asn Gln Tyr Leu Val Gly Ser Gln
                1125                1130                1135
Leu Pro Cys Glu Pro Glu Pro Asp Val Ala Val Leu Thr Ser Met Leu
            1140                1145                1150
Thr Asp Pro Ser His Ile Thr Ala Glu Thr Ala Lys Arg Arg Leu Ala
        1155                1160                1165
Arg Gly Ser Pro Pro Ser Leu Ala Ser Ser Ser Ala Ser Gln Leu Ser
1170                1175                1180
Ala Pro Ser Leu Lys Ala Thr Cys Thr Thr His His Asp Ser Pro Asp
1185                1190                1195                1200
Ala Asp Leu Ile Glu Ala Asn Leu Leu Trp Arg Gln Glu Met Gly Gly
                1205                1210                1215
Asn Ile Thr Arg Val Glu Ser Glu Asn Lys Val Val Ile Leu Asp Ser
            1220                1225                1230
Phe Asp Ser Leu Arg Ala Glu Glu Asp Glu Arg Glu Ile Ser Val Glu
        1235                1240                1245
Ala Glu Ile Leu Arg Arg Ser Lys Lys Phe Pro Pro Ala Met Pro Ile
    1250                1255                1260
Trp Ala Arg Pro Asp Tyr Asn Pro Pro Leu Leu Glu Ser Trp Lys Asp
1265                1270                1275                1280
Pro Asp Tyr Val Pro Pro Val His Gly Cys Pro Leu Pro Pro Thr
                1285                1290                1295
Lys Ala Pro Pro Ile Pro Pro Arg Arg Lys Lys Thr Val Val Leu
            1300                1305                1310
Thr Glu Ser Thr Val Ser Ser Ala Leu Ala Glu Leu Ala Ser Lys Thr
        1315                1320                1325
Phe Gly Ser Ser Gly Ser Ser Ala Val Asp Ser Gly Thr Ala Thr Ala
    1330                1335                1340
Pro Pro Asp Gln Ala Ser Asp Asp Gly Asp Lys Glu Ser Asp Val Glu
1345                1350                1355                1360
Ser Tyr Ser Ser Met Pro Pro Leu Glu Gly Glu Pro Gly Asp Pro Asp
                1365                1370                1375
Leu Ser Asp Gly Ser Trp Ser Thr Val Ser Glu Glu Ala Gly Glu Asp
            1380                1385                1390
Val Val Cys Cys Ser Met Ser Tyr Thr Trp Ser Arg Leu Asp Lys Ser
        1395                1400                1405
Lys Val Ile Asn Ser Ala Leu Glu Leu Leu Asn Asp Val Gly Ile Glu
    1410                1415                1420
Gly Leu Thr Thr Arg Lys Leu Ala Gln Lys Leu Gly Val Glu Gln Pro
1425                1430                1435                1440
Thr Leu Tyr Trp His Val Lys Asn Lys Arg Ala Leu Leu Asp Ala Leu
                1445                1450                1455
Ala Ile Glu Met Leu Asp Arg His His Thr His Phe Cys Pro Leu Glu
            1460                1465                1470
Gly Glu Ser Trp Gln Asp Phe Leu Arg Asn Asn Ala Lys Ser Phe Arg
        1475                1480                1485
Cys Ala Leu Leu Ser His Arg Asp Gly Ala Lys Val His Leu Gly Thr
    1490                1495                1500
```

-continued

Arg Pro Thr Glu Lys Gln Tyr Glu Thr Leu Glu Asn Gln Leu Ala Phe
1505                1510                1515                1520

Leu Cys Gln Gln Gly Phe Ser Leu Glu Asn Ala Leu Tyr Ala Leu Ser
            1525                1530                1535

Ala Val Gly His Phe Thr Leu Gly Cys Val Leu Glu Asp Gln Glu His
        1540                1545                1550

Gln Val Ala Lys Glu Glu Arg Glu Thr Pro Thr Thr Asp Ser Met Pro
    1555                1560                1565

Pro Leu Leu Arg Gln Ala Ile Glu Leu Phe Asp His Gln Gly Ala Glu
1570                1575                1580

Pro Ala Phe Leu Phe Gly Leu Glu Leu Ile Ile Cys Gly Leu Glu Lys
1585                1590                1595                1600

Gln Leu Lys Cys Glu Ser Gly Ser Ala Tyr Ser Arg Ala Arg Thr Lys
            1605                1610                1615

Asn Asn Tyr Gly Ser Thr Ile Glu Gly Leu Leu Asp Leu Pro Asp Asp
        1620                1625                1630

Asp Ala Pro Glu Glu Ala Gly Leu Ala Ala Pro Arg Leu Ser Phe Leu
        1635                1640                1645

Pro Ala Gly His Thr Arg Arg Leu Ser Thr Ala Pro Pro Thr Asp Val
    1650                1655                1660

Ser Leu Gly Asp Glu Leu His Leu Asp Gly Glu Asp Val Ala Met Ala
1665                1670                1675                1680

His Ala Asp Ala Leu Asp Asp Phe Asp Leu Asp Met Leu Gly Asp Gly
            1685                1690                1695

Asp Ser Pro Gly Pro Gly Phe Thr Pro His Asp Ser Ala Pro Tyr Gly
        1700                1705                1710

Ala Leu Asp Met Ala Asp Phe Glu Phe Glu Gln Met Phe Thr Asp Ala
    1715                1720                1725

Leu Gly Ile Asp Glu Tyr Gly Gly
  1730                1735

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: forward
      primer complementary to 5' end of HCV NS3 gene

<400> SEQUENCE: 3
ggcgctagcg cgcccatcac ggcctac                                       27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: reverse
      primer complementary to 3' end of NS4A domain including
      NS4A/4B cleavage site

<400> SEQUENCE: 4
ggctctagag taagggaggt gtgaggc                                       27

<210> SEQ ID NO 5
<211> LENGTH: 37
<212> TYPE: DNA
<213> ORGANISM: Artificial Sequence
<220> FEATURE:

```
<223> OTHER INFORMATION: Description of Artificial Sequence: reverse
      primer complementary to 3' end of NS4A domain including
      mutated NS4A/4B cleavage site

<400> SEQUENCE: 5
ggctctagag taagggaggt gtgaggggcg ctcttcc                              37

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: reverse
      primer complementary to 3' end of NS4A including last 6 codons of
      NS5A

<400> SEQUENCE: 6
gcagcagacg acgtcctcga attcccggta gaggac                               36

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: reverse
      primer complementary to NS5A/5B cleavage site

<400> SEQUENCE: 7
ggctctagac catgtgtagg acatcgagca gcagacgacg tcctc                     45

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: reverse
      primer complementary to mutated 5A/5B cleavage site

<400> SEQUENCE: 8
ggctctagac catgtgtagg acataggcct gcagacgacg tcctc                     45

<210> SEQ ID NO 9
<211> LENGTH: 77
<212> TYPE: DNA
<213> ORGANISM: Artificial Sequence
<220> FEATURE:
<223> OTHER INFORMATION: Description of Artificial Sequence: reverse
      primer for NS3 S1165A mutant

<400> SEQUENCE: 9
cccccgggtg cacacagctg cccggaagat gcccacaacg gccccgaagg gcagagcagt     60
gggccacccg cagagcc                                                    77
```

SURROGATE CELL-BASED SYSTEM AND METHOD FOR ASSAYING THE ACTIVITY OF HEPATITIS C VIRUS NS3 PROTEASE

RELATED APPLICATIONS

This application is a continuation of prior U.S. application Ser. No. 09/563,899 filed May 3, 2000, now abandoned, which claims, as does the present application priority to U.S. provisional application No. 60/132,360 filed May 4, 1999, the disclosures of all of which are incorporated by reference in their entirety.

FIELD OF THE INVENTION

The present invention relates to a mammalian cell culture system and method for assaying hepatitis C virus (HCV) NS3 protease activity and inhibition thereof. More particularly this invention relates to a recombinant molecule, a transfected host mammalian cell assay system and a method for measuring NS3 protease activity and inhibition thereof by candidate anti-HCV compounds.

BACKGROUND OF THE INVENTION

Hepatitis C virus (HCV) is the major etiological agent of post-transfusion and community-acquired non-A non-B hepatitis worldwide. It is estimated that over 100 million people worldwide are infected by the virus. A high percentage of carriers become chronically infected and many progress to chronic liver disease, so called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Various clinical studies have been conducted with the goal of identifying pharmaceutical compounds capable of effectively treating HCV infection in patients afflicted with chronic hepatitis C. These studies have involved the use of interferon-alpha, alone and in combination with other antiviral agents such as ribavirin. Such studies have shown that a substantial number of the participants do not respond to these therapies, and of those that do respond favorably, a large proportion were found to relapse after termination of treatment. To date there are no broadly effective antiviral compounds for treatment of HCV infection. HCV is an enveloped positive strand RNA virus in the Flaviviridae family.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce structural and non-structural (NS) proteins. The structural proteins (C, E1, E2 and E2-p7) comprise polypeptides that constitute the virus particle. The non-structural proteins (NS2, NS3, NS4A, NS4B, NS5A, NS5B) encode for enzymes or accessory factors that catalyze and regulate the replication of the HCV RNA genome. Processing of the structural proteins is catalyzed by host cell proteases. The generation of the mature non-structural proteins is catalyzed by two virally encoded proteases. The first is the NS2–3 zinc-dependent metalloprotease which auto-catalyses the release of the NS3 protein from the polyprotein. The released NS3 contains a serine protease domain at the N-terminal and catalyzes the remaining cleavages from the polyprotein. The released NS4A protein has at least two roles. First, forming a stable complex with NS3 protein and assisting in the membrane localization of the NS3/NS4A complex (Kim et al., 1999) and second, acting as a cofactor for NS3 protease activity. This membrane-associated complex, in turn catalyzes the cleavage of the remaining sites on the polyprotein, thus effecting the release of NS4B, NS5A and NS5B. The C-terminal segment of the NS3 protein also harbors nucleoside triphosphatase and RNA helicase activity. NS5B is an RNA-dependent RNA polymerase that is involved in the replication of HCV.

The N-terminal 180 amino acids of the NS3 protein is a trypsin-like serine protease that mediates as a first step the auto-cleavage of NS3/4A. The membrane associated NS3/4A complex further cleaves NS4A/4B, NS4B/5A, and NS5A/NS5B junctions to release the viral enzymes considered essential for viral replication. The complexing of NS3/NS4A is an important step in the sequential downstream processing of the polyprotein. The NS3 protein is the most thoroughly characterized HCV protein. Kinetic parameters for cleavage of all the processing sites have been described. Both the N-terminal protease and C-terminal helicase domains have been independently crystallized and high resolution three-dimensional models exist for these structures.

NS3 protease activity is an attractive target for drug discovery. Enzymatic studies have shown that peptides based on the N-terminal product of the NS5A/5B cleavage site are competitive inhibitors of the enzyme. These peptides have served as a useful starting point in medicinal chemistry efforts to rationally design NS3 protease inhibitors as clinically effective anti-HCV compounds.

Due to the high incidence of HCV and the consequences of HCV infections, finding therapeutic compounds against HCV has become important. To that end, efforts to discover compounds against HCV have necessitated developing assay systems for screening and selecting anti-HCV compounds.

To date, a convenient cell culture replication system for the HCV virus is not available. This deficiency has restricted most of the HCV inhibitor screening to in-vitro enzymatic assays and indirect surrogate cell-based assay (Lohmann et al. (1999)). This has severely limited the evaluation of potential anti-HCV compounds in cell culture.

Hirowatari et al. (1995) describes the co-transfection of a first plasmid containing the NS2/NS3 domain fused to the NS5A/NS5B cleavage site (substrate for NS3) and the transactivator Tax 1, and a second plasmid containing a reporter gene whose expression is dependent on Tax 1 transactivation. The NS5A/5B site is cleaved by the expressed NS2 or NS3 protease activity thereby releasing Tax 1 to transactivate the reporter gene on the second plasmid. Thus, the amount of the expressed reporter gene is a measure of NS2 or NS3 proteolytic activity. One of the drawbacks is that this system does not distinguish between the activities of the NS2 metalloprotease and NS3 protease activity. In addition, this system does not allow the measure of protease activity of the NS3 protein when complexed with the NS4A domain, a complex that enhances the specificity of the protease. This assay also does not allow one to measure the protease activity in a system that is closest to the natural context of polyprotein processing. Finally, a further drawback resides in the fact that this system is semi-quantitative, therefore not suitable for quantitative high-throughput screening.

Overton, H. et al. (1995), teach a baculovirus-expressed HCV NS3 activity in insect cells. A series of baculovirus constructs designed to express NS3 protease activity and different substrates are described. Constructs encoding partial NS2/NS3 and NS3/NS4A/NS4B are transfected into an insect cell line. Additional viral constructs encoding NS3 to NS5A and NS5A/5B are transfected alone or together with one of the above constructs. The expressed and cleaved products are visualized immunologically by Western analysis. Some of the deficiencies in this system relate to the use of an insect instead of a mammalian cell line, as well as the requirement for viral infection, an event that may further disrupt the normal functions of the cell. This system also employs the T7 polymerase expression system, a system that is not necessary for the system of the present invention. In addition, the method for detection of the cleavage products is lengthy, difficult to quantify with precision and not amenable to high throughput scale.

Song et al., (1996) described a protease assay system utilizing a lexA-GAL4 fusion protein in yeast. The authors describe inserting the NS3 protease and a cleavage site between the lexA-DNA binding domain and the transcriptional activating domain of GAL4. Cleavage of that site by NS3 protease renders GAL4 transcriptionally inactive leading to the inability of the transformed yeast to synthesize β-galactosidase. This system lacks the NS4A and does not reproduce processing in the context of the HCV polyprotein.

Cho, Y. G. et al., (1997), teach an assay using the sindbis viral replication system. This hybrid virus construct encodes the HCV NS3/NS4A protease region linked to SIN core proteins by the NS4A/NS4B cleavage sequence. Assembly of viral particles in a mammalian cell line is dependent on the processing of the NS4A/4B cleavage site. One major drawback of this system resides in that the HCV protease activity produces chimeric virus that induce cytopathic morphological changes in cells. Measurement of the pH change of the media constitutes a semi-quantitative way of measuring these changes at best. A further drawback in this system is that the sindbis core protein contains a natural serine protease cleavage site similar to the NS3 site thus making this system of limited use for screening potential protease inhibitors. Cho, Y. G. et al., (1998), teach an expression vector encoding the NS3/NS4A region and the NS4A/4B cleavage site fused to the SEAP (secreted alkaline phosphatase) gene, transfected into a mammalian cell line. Cleavage of the NS4A/4B site by NS3 protease releases SEAP protein into the media. The amount of SEAP protein in the media is a measure of NS3 protease activity. One drawback of this system lies in the fact that the reporter molecule is directly fused to the substrate protein and may therefore affect the natural conformation of viral complex proteins (NS3/NS4A). A further major drawback resides in the fact that the amount of reporter protein secreted is in direct proportion to the amount of protein expressed and cleaved in the system (1 substrate molecule cleaved=1 reporter molecule secreted). Since the HCV polyprotein is a system that is expressed at very low levels (even in its natural context), the signal observed is too low to be carried out on a large screening scale.

WO 98/00548, describes hybrid viruses comprising a picornavirus, preferably poliovirus, HCV NS3 protease domain and a single NS3 protease target site. These chimeric viruses are engineered such that the proteolytic processing activity of HCV NS3 is essential for viral viability and proliferation. Various hybrids, each having a different NS3 cleavage site (NS5A/NS5B, NS4A/NS4B or NS4B/NS5A) are taught. Viability, is measured by the viral titer using the plaque assay on HeLa monolayer cells. Once again this system does not provide quantifiable means for screening large numbers of potential inhibitors in a high throughput fashion and does not provide for screening of NS3 protease activity in the natural context of the polyprotein segment.

U.S. Pat. No. 5,861,267 by Vertex discloses a method for assaying HCV NS3 protease that utilizes expression of the NS3/NS4A region and the NS4A/NS4B cleavage site fused to the secreted IL-1β reporter (interleukin-1β). Cleavage at the NS4A/4B site by the NS3 protease releases IL-1β into the medium which permits a direct measure of NS3 protease activity. This system examines inhibition of NS3 cleavage at a cleavage site adjacent to the NS3/NS4A complex, a situation that does not represent or replicate the authentic conditions of multiple sites of polyprotein processing present in infected cells. In addition, this system provides a reporter system where the signal measured is in direct proportion to the amount of protein expressed in the system and the amount of protein cleaved, once again giving rise to a signal too low to be carried out on a large screening scale.

WO 00/08469 by Agouron discloses a further system comprising a protease-reporter construct consisting of the NS2 metalloprotease, the NS3 protease, the NS4A co-factor and different variations of truncated NS4B and 5A, preceding the NS5A/5B cleavage site. This system however, does not disclose the importance of having a full polyprotein for optimizing the NS3 protease activity/specificity. In addition, this system requires infection by a vaccinia virus vector, a factor that mitigates the host cell integrity and may affect the mechanism of cis or trans protease cleavage during polyprotein processing events in the assay. A further drawback of using the vaccinia expression lies in the fact that the cells in the assay become necrotic after about 24 hours, thereby limiting the use of this assay for longer term kinetic assays.

WO 00/12727 by Vertex discloses a system having a fusion protein comprising a ligand binding domain, a DNA binding domain that can bind to a ligand-response element causing the VP16 activation domain to regulate expression of a reporter gene. A NS5A/5B cleavage site is inserted within that fusion protein and modulates the reporter gene expression upon cleavage by the NS3/4A protease which is expressed from a separate construct. Once again, this system does not disclose the importance of having a full polyprotein for optimizing the NS3 protease activity/specificity.

It has therefore become important to develop an assay for screening large numbers of anti-HCV compounds, with the capacity to scale up to a high throughput system. The present invention therefore provides an assay that is easy to perform, reliable, sensitive and reproducible on large scale.

It is therefore the purpose of this invention to provide a cell-based system and assay having improved sensitivity for measuring inhibition of the HCV NS3 protease activity, this assay being designed to concurrently test the protease activity in a construct that reproduces as much as possible the NS3 polyprotein processing events occurring in infected cells in the course of HCV disease.

The present application refers to a number of documents, the content of which is herein incorporated by reference.

SUMMARY OF THE INVENTION

Thus, the present invention concerns the development of a cell-based assay system having improved sensitivity to HCV NS3 protease activity when compared to known assays and which is useful for screening test compounds capable of modulating (particularly inhibiting) HCV NS3 protease activity.

This invention provides a first construct comprising a transactivator domain joined downstream of the NS3–5 domains of HCV under the control of a non-cytopathic viral promoter system. A second construct is also provided that comprises a reporter gene under the control of an operator sensitive to the binding of the transactivator.

The NS3–5 domains encodes the NS3 polyprotein which comprises: the NS3 protease, followed by the NS4A co-factor, the NS4B and NS5A proteins (including any derivative, variant or fragment thereof), terminated by the NS5B protein (including any derivative, variant or fragment thereof) sufficient to constitute a NS5A/5B cleavage site. The transactivator, when expressed and released from the polyprotein initiates transcription and expression of the reporter gene that is measurable.

The advantages of this system are manyfold including the fact that, the NS4A co-factor domain, when expressed, remains embedded in the endoplasmic reticulum membrane thereby anchoring the NS3 protease when complexed with NS4A and reducing background signal (by preventing non-specific translocation) when none of the downstream cleavage sites of the polyprotein is processed.

The advantages of this system also reside in several levels of amplification of the signal measured. Applicant believes that a first level of amplification lies in the fact that the polyprotein sensibly reproduces the native conformation of the polyprotein and natural processing events occurring during human infection. This enhances the activity of the NS3 protease cleavage as well as its specificity. The signal translocation to the nucleus and reporter expression is therefore more specific and background noise reduced to a minimum acceptable for high throughput screening assays.

The use of a transactivator system also provides a second level of amplification that further increases the signal output.

Finally, this transactivator system, being sensitive to antibiotic presence, provides an internal "built-in" negative control that allows the measure of inherent background noise of the assay thereby ensuring specificity of both the assay and of the test compounds.

Thus, the present invention provides a cell-based assay having the ability to measure NS3 protease inhibition in a system that closely mimics processing of HCV non-structural proteins in context that substantially reproduces the natural infection process. The mammalian cell-based system of the present invention is highly sensitive, demonstrating increased signal/noise ratio when compared to other known assays. Therefore, the assay using this system an be easily scaled up to a high throughput screening system.

Therefore, in accordance with a first embodiment of the present invention, there is provided a surrogate cell-based system to evaluate the protease activity of Hepatitis C virus NS3 protease comprising:

a) a first chimeric DNA molecule comprising:
   i) a non-cytopathic expression system capable of inducing expression of said first chimera upon transfection in a mammalian cell; and
   ii) a HCV recombinant DNA molecule operably linked to said expression system; said HCV DNA molecule encoding the NS3–5 polyprotein comprising:
      an active NS3 protease domain,
      a NS4A domain sufficient to allow embedding in the ER membrane upon translation and acting as co-factor for the NS3 protease activity,
      NS4B and NS5A domains, including any derivative, variant or fragment thereof, and
      NS5B protein including any derivative, variant or fragment thereof, sufficient to provide a NS5A/5B cleavage site for said NS3 protease;
   iii) and a transactivator domain fused downstream of said HCV DNA molecule, said transactivator domain encoding a transactivator molecule capable of initiating expression of a reporter gene;
b) and a second chimeric DNA molecule encoding said reporter gene co-joined to an operon responding to said transactivator molecule;

whereby expression of said first recombinant molecule leads to the production of a fusion polyprotein anchored to the endoplasmic reticulum of said mammalian cell, said anchored protein capable of being cleaved by said protease thereby allowing translocation of said transactivator domain for inducing expression of said reporter gene as a means to evaluate said protease activity.

In a second embodiment, the invention encompasses the recombinant DNA molecules useful in this system and any fragment, variant and derivative thereof.

In a third embodiment, the invention encompasses recombinant proteins produced from the recombinant DNA molecules of the invention.

In a fourth embodiment the invention also encompasses vectors comprising any of those recombinant DNA molecules.

In a fifth embodiment, the present invention encompasses eukaryotic host cells transfected with these vectors.

In a sixth embodiment, the invention encompasses a method for assaying NS3 protease activity by using the recombinant molecules and transfected host cells of the invention, this method being also useful for identifying potential inhibitors thereof.

Other objects, advantages and features of the present invention will become more apparent upon reading of the following non-restrictive description of the preferred embodiments with reference to the accompanying drawings which is exemplary and should not be interpreted as limiting the scope of the invention.

BRIEF DESCRIPTION OF THE DRAWINGS

FIG. 1 shows a schematic overview of a two plasmid-based assay in which NS3 protease activity mediates luciferase activation. The scheme shows the recombinant HCV non-structural precursor polyprotein co-joined to a tetracycline transactivator domain (tTA) via the 5A/5B target cleavage site. In an initial processing step, NS4A is cleaved "in cis" by NS3, forming a complex as shown by the overlapping circles of NS3/NS4A. This complex, which is in association with the endoplasmic reticulum membrane (ER), catalyzes the cleavage of the downstream target sites (4A/4B, 4B/5A, and 5A/5B) thereby releasing the tTA domain from the recombinant molecule. Once liberated the tTA domain migrates to the nucleus and transactivates the expression of the reporter gene, in this case, luciferase. Thus, NS3 protease activity and cleavage downstream of the NS3/4A cleavage site is essential for the expression of luciferase.

Figure 4:

The middle panel shows that luciferase transactivation does not occur in the absence of released tTA domain. Possible mechanisms for the non-release of tTA may be: lack of NS3 protease activity (by mutation as in this case), or blockage at the downstream target cleavage sites.

The bottom panel shows that luciferase transactivation does not occur in the presence of tetracycline. Although the NS3 polyprotein is cleaved and the tTA domain is translocated to the nucleus, tetracycline binds to the tTA and prevents DNA binding and expression of the reporter gene thereby providing a reliable internal control for measuring the background activity of luciferase.

FIG. 2 shows the schematics of three different families of chimeras comprising different portions of the HCV polyprotein fused to the tetracycline transactivator (tTA) with their respective controls. The DNA encoding the HCV segment of these chimeras was cloned as an Xba 1 fragment into the Nhe 1 and Xba 1 sites of pUHD15-1 to generate the tTA chimeras.

FIG. 2A shows the first chimera in the first family (construct A), in which the recombinant molecule comprises the HCV full length NS3 protein (including both the protease and helicase domains), full length NS4A (including the last six amino acids designated as P6 to P1), the first six amino acid of NS4B designated as P1' to P6' fused to the tTA protein. The P6 to P1 and the P1' to P6' amino acids straddle the 4A/4B cleavage site as shown by the dark arrow.

FIG. 2B shows the second chimera in the first family (construct B), which is the same recombinant molecule as in 2A with the exception that the NS3 protein is mutated at amino acid 1165 from serine to alanine (S1165A). This construct serves as a control, since the mutation completely obviates NS3 protease activity.

FIG. 2C shows the third chimera in the first family (construct C), which is the same chimera as in 2A with the exception that the two amino acids designated P1 and P1' flanking the NS4A/4B cleavage site are altered from cysteine and alanine to arginine and proline, respectively. These changes obviate cleavage at this site. This construct serves as a control for the cleavage site.

FIG. 2D shows the first chimera in the second family (construct D), in which the construct is the same as the chimera in 2A but where the amino acid sequence (P6–P6') straddling the NS4A/NS4B cleavage site is replaced with the amino acid sequence (P6–P6') defining the NS5A/NS5B cleavage site.

FIG. 2E shows the second chimera in the second family (construct E), which is the same construct as in 2D with the exception that the NS3 protease is inactivated by mutating the amino acid serine to alanine (S1165A). This construct serves as a control for the second chimera.

FIG. 2F shows the third chimera in the second family (construct F), which is the same construct as in 2D with the exception that the two amino acids designated P1 and P1' flanking the NS5A/5B cleavage site are altered from cysteine and serine to arginine and proline, respectively. These changes obviate cleavage at this site. This construct serves as a control for the 5A/5B cleavage site.

FIG. 2G shows the first chimera in the third family (construct G), in which the recombinant molecule comprises: the region between full length NS3 protein, full length NS4A, NS4B and NS5A proteins, and a partial NS5B protein (consisting of the first six amino acids designated P1' to P6'), fused to the tTA protein. The full length NS5A and the P1' to P6' of 5B straddle the 5A/5B target cleavage site as shown by the dark arrow.

FIG. 2H shows the second chimera in the third family (construct H), which is the same recombinant molecule as in 2G with the exception that the NS3 protease is inactivated by mutating the amino acid serine to alanine (S1165A). This construct serves as a negative control for NS3 protease activity.

FIG. 2I shows the third chimera in the third family (construct I), which is the same recombinant molecule as in 2G with the exception that the two amino acids designated P1 and P1' flanking the NS5A/5B cleavage site are altered from cysteine and serine to arginine and proline, respectively. These changes obviate cleavage at this site. This construct serves as a control for the 5A/5B target cleavage site.

FIG. 3 shows the results of Western blot analyses. The chimeras described in FIGS. 2A, 2B and 2C inserted into the expression plasmid pCR3.1 by PCR amplification and TA cloning (Invitrogen, CA, USA), are transiently transfected into the human embryonic kidney cell line 293 along with the recombinant T7 vaccinia virus (vvT7-3) harboring the T7 RNA polymerase. The transfected and infected cells were grown and cellular protein extracted, electrophoresed, blotted and probed.

FIG. 3A shows the results when the blot is probed with a polyclonal antibody to NS3 protein. Lanes A, B and C, correspond to the constructs described in 2A, 2B and 2C, respectively, lane "-" denotes a control of mock 293 transfected cells. Lanes A and C demonstrate the presence of mature NS3 protein (NS3), whereas lane B representing the construct with the S1165A mutation, demonstrates the presence of pre-processed NS3 (pre) but does not appear to have any mature NS3 protein.

FIG. 3B shows the results when the blot is probed with a polyclonal antibody to NS4A. Lane A demonstrates the presence of mature NS4A protein (NS4A), lane B representing construct 2B with the S1165A mutation does not appear to have any mature NS4A protein, similarly lane C representing construct C with the mutated cleavage site does not appear to have mature NS4A protein. In order to visualize mature NS4A protein which consists of 54 amino acids, cellular extracts were resolved on 16.5% SDS PAGE Tricine gel transferred to a membrane and probed with NS4A polyclonal antibody The resultant band is shown in the bottom panel.

FIG. 4 shows the results of Western blot analyses. The chimeras described in FIGS. 2D, 2E and 2F inserted into the expression plasmid pCR3.1 by direct TA cloning of PCR products, are transiently transfected into the mammalian host cell line 293 along with the recombinant T7 vaccinia virus (vvT7-3) harboring the T7 RNA polymerase. The transfected cells are grown and cellular protein is extracted, electrophoresed, blotted and probed. The results show the blot probed with a polyclonal antibody to NS3 protein. Lanes D, E and F, correspond to the constructs described in 2D, 2E and 2F, respectively, lane "-" denotes a control of mock 293 transfected cells. Lanes D and F demonstrate the presence of mature NS3 protein (NS3), whereas lane E representing the construct with the S1165A mutation demonstrates the presence of pre-processed NS3 (pre) but does not appear to have any mature NS3 protein.

FIG. 5 shows the results of Western blot analyses. The chimeras described in FIGS. 2G, 2H and 2I inserted into the expression plasmid pCR3.1 by direct TA cloning of PCR products, are transiently transfected into the mammalian host cell line 293 along with the recombinant T7 vaccinia virus (vvT7-3) harboring the T7 RNA polymerase. The transfected cells are grown and cellular protein is extracted, electrophoresed, blotted and probed.

FIG. 5A shows the results of the blot probed with a polyclonal antibody to NS3 protein. Lanes G, H and I, correspond to the constructs described in 2G, 2H and 2I, respectively, lane "-" denotes a control of mock 293 transfected cells. Lanes G and I demonstrate the presence of mature NS3 protein (NS3), whereas lane H representing the construct with the S1165A mutation does not appear to have any mature NS3 protein.

FIG. 5B shows the results of the Western blot probed with a polyclonal antibody to NS4A protein. Lanes G, H and I, correspond to the constructs described in 2G, 2H and 2I, respectively, lane "-" denotes a control of mock 293 transfected cells. Lanes G and I demonstrate the presence of mature NS4A protein (NS4A), whereas lane H representing the construct with the S1165A mutation does not appear to have any mature NS 4A.

FIG. 5C shows the results of the Western blot probed with a polyclonal antibody to NS5A protein. Lanes G, H and I, correspond to the constructs G, H and I, respectively, lane "-" denotes a control of mock 293 transfected cells. Lane G demonstrates the presence of mature NS5A protein (NS5A), whereas lane H representing the construct with the S1165A mutation does not appear to have any mature NS5A protein. Similarly lane I representing construct I with the mutated NS5A/5B cleavage site does not appear to have mature NS5A protein and the unprocessed NS5A-tTA fusion protein is detected as a ≈90kDa product.

FIG. 6 shows the results of the luciferase assay performed on extracts of 293 cells co-transfected with one of the constructs A to I and the pUHC13-3 reporter plasmid. The luciferase activity is a measure of photon counts per second. The designations A to I correspond to the constructs described in FIGS. 2A to 2I, respectively. The controls B, E and H are defective in the protease active site whereas the controls C, F and I have a defective cleavage site. The results of this assay indicate that luciferase activity is dependent on both, an active NS3 protease and a functional cleavage site. The results further indicate that construct G demonstrates greater luciferase activity than constructs A or D. These values are an average of two experiments.

Figure 7:
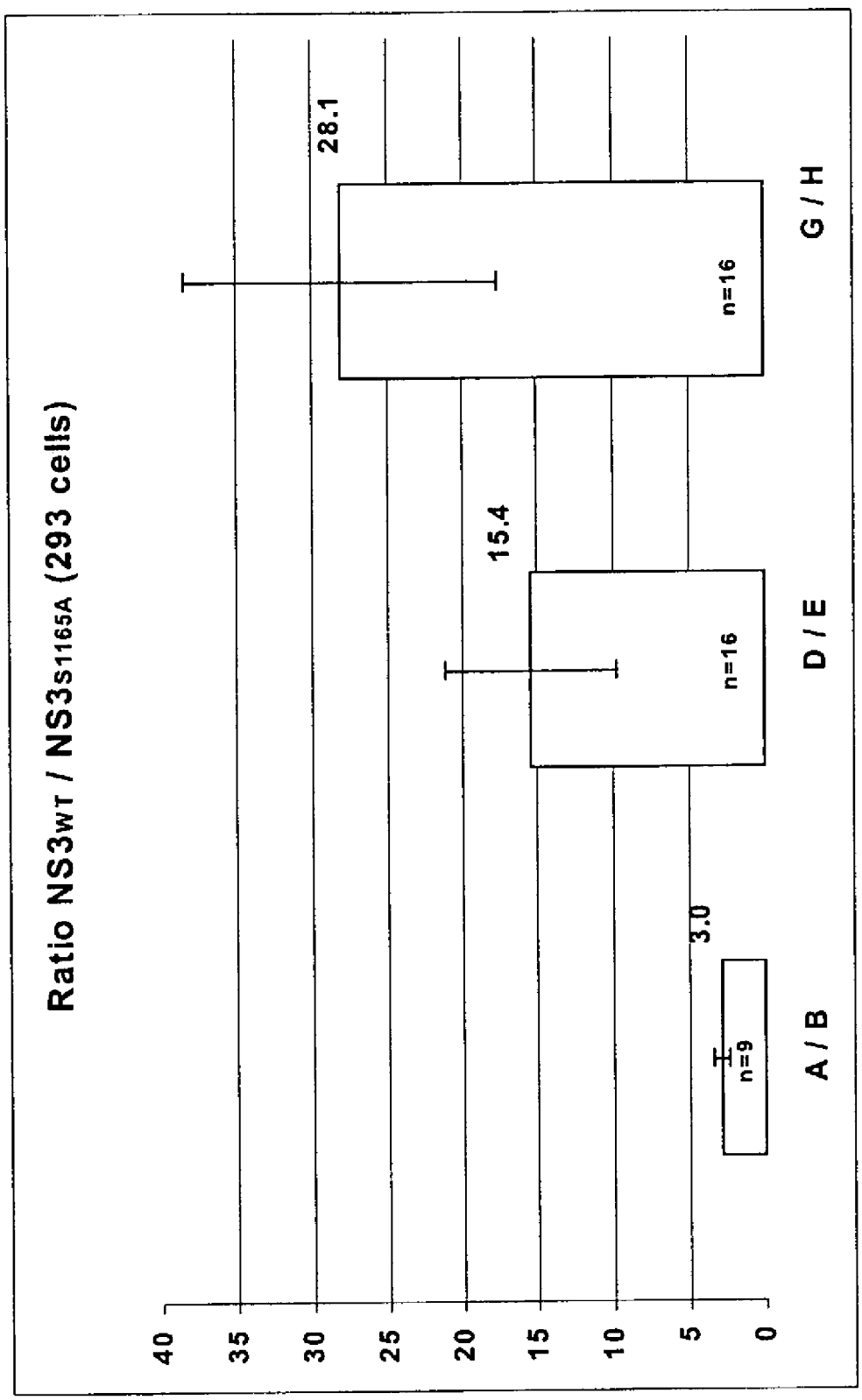

FIG. 7 shows the ratio of luciferase activity produced by constructs A, D and G over their respective active site mutants B, E and H using the values shown in FIG. 6. The results show that the ratio of G/H is approximately 9 and 2 fold greater than A/B and D/E, respectively. Construct G, with the longest stretch of HCV non-structural region comprising full length NS3, NS4A, NS4B and NS5A, and partial NS5B, produces the greatest NS3-dependent luciferase response. The results are an average of n experiments.

Figure 8:
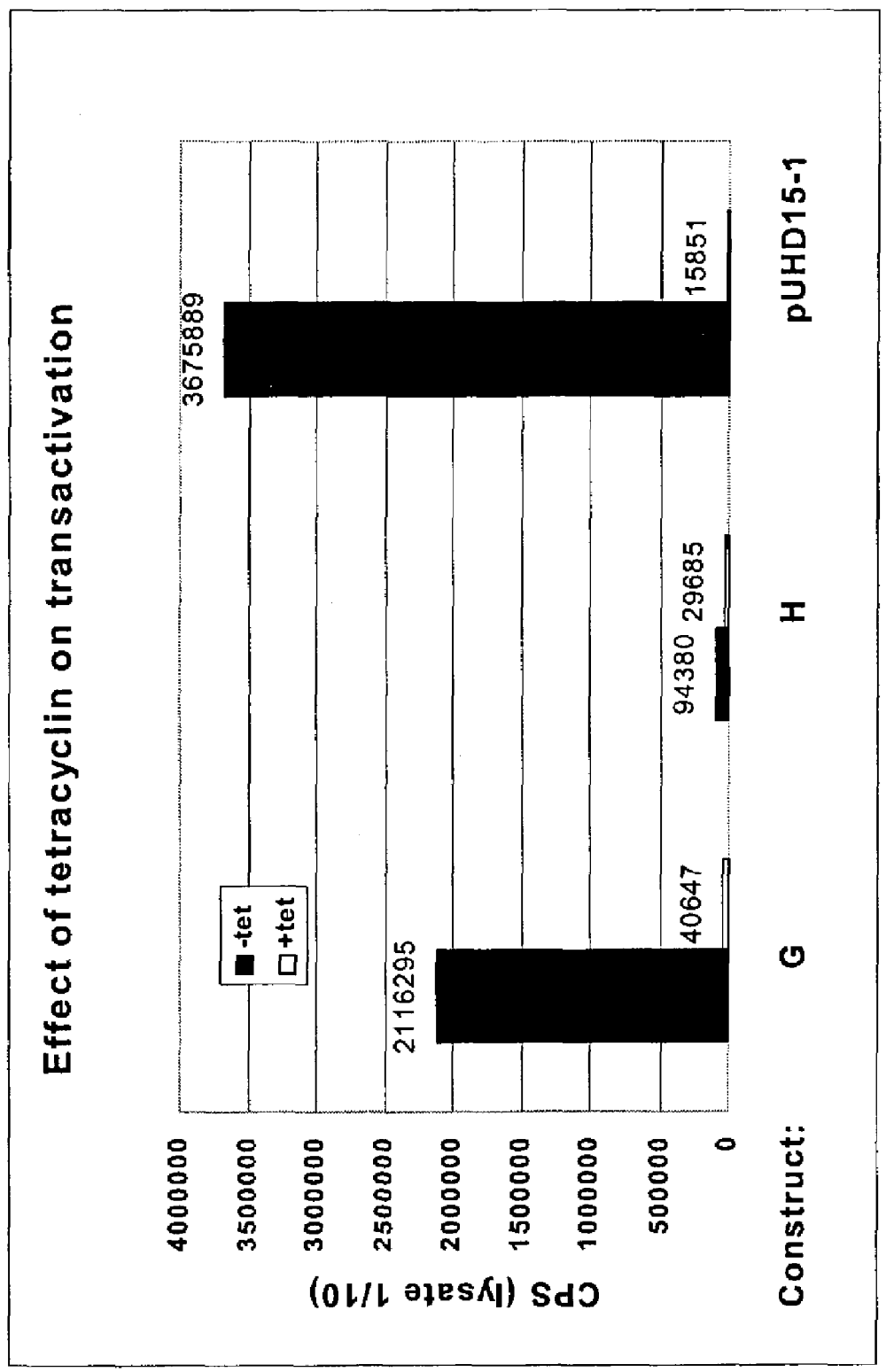

FIG. 8 shows the effect of tetracycline on the tetracycline responsive transcriptional trans-activator. Expression of the luciferase reporter gene is controlled by NS3 processing of a tetracycline responsive transcriptional trans-activator. Luciferase assay performed on extracts of 293 cells co-transfected with construct G or H, or the positive control tTA-producing plasmid (pUHD15-1), and the pUHC13-3 plasmid containing the luciferase reporter. Closed and open bars indicate the absence and presence of tetracycline, respectively. Note that construct G produces a tetracycline controlled signal; inactivation of the NS3 protease activity (in construct H) abolishes this signal.

Figure 9:
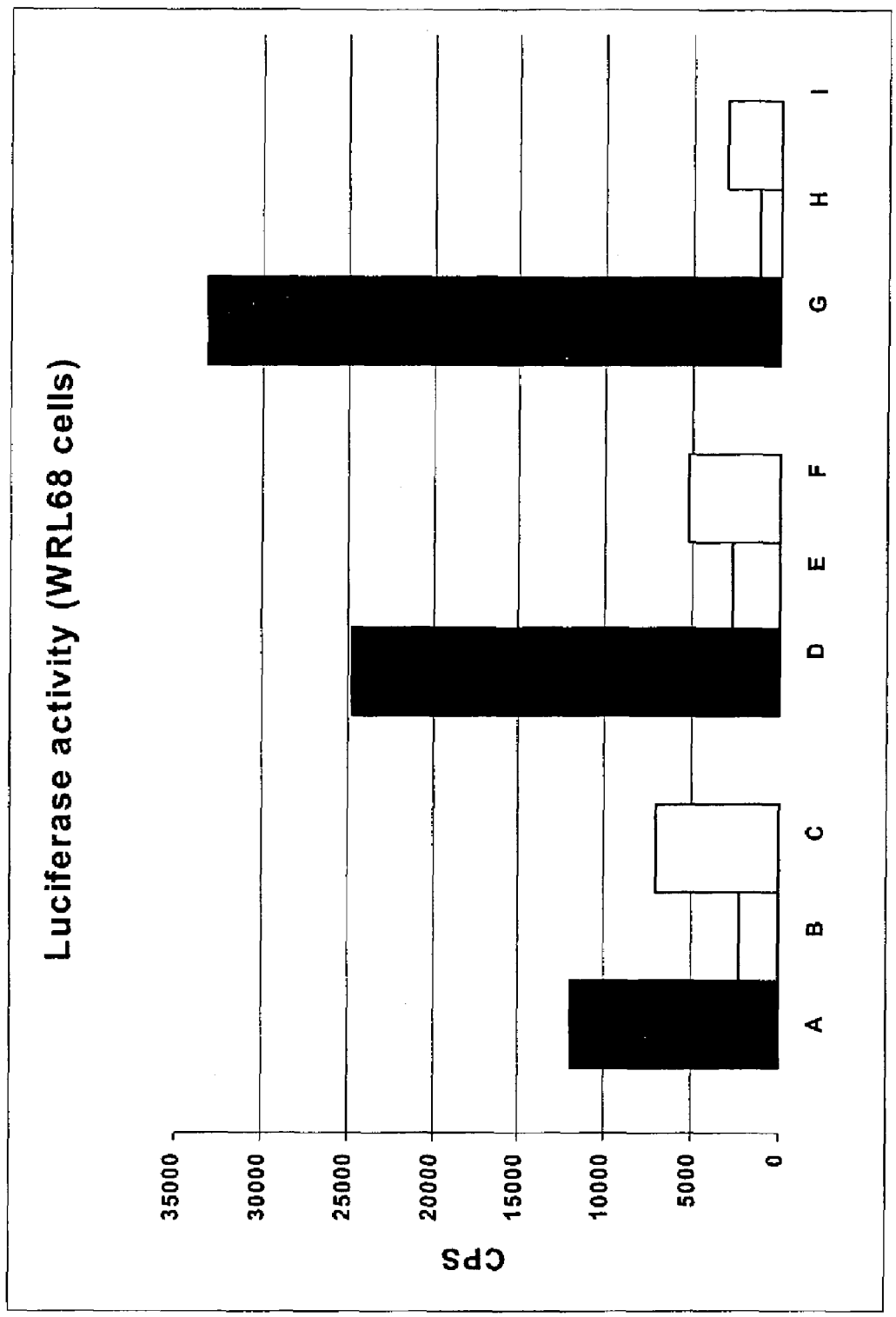

FIG. 9 shows the results of the luciferase assay performed on extracts of the liver cell line WRL68 co-transfected with one of the constructs A to I and the pUHC13-3 reporter plasmid. The luciferase activity is a measure of photon counts per second. The controls B, E and H are defective in the protease active site. The controls C, F and I have a defective cleavage site and thus do not have a functional (cleavable) NS3 protease cleavage site. The results of this assay indicate that luciferase activity is dependent on both, an active NS3 protease and a functional cleavage site. The results further indicate that construct G demonstrates greater luciferase activity than constructs A or D.

Figure 10:
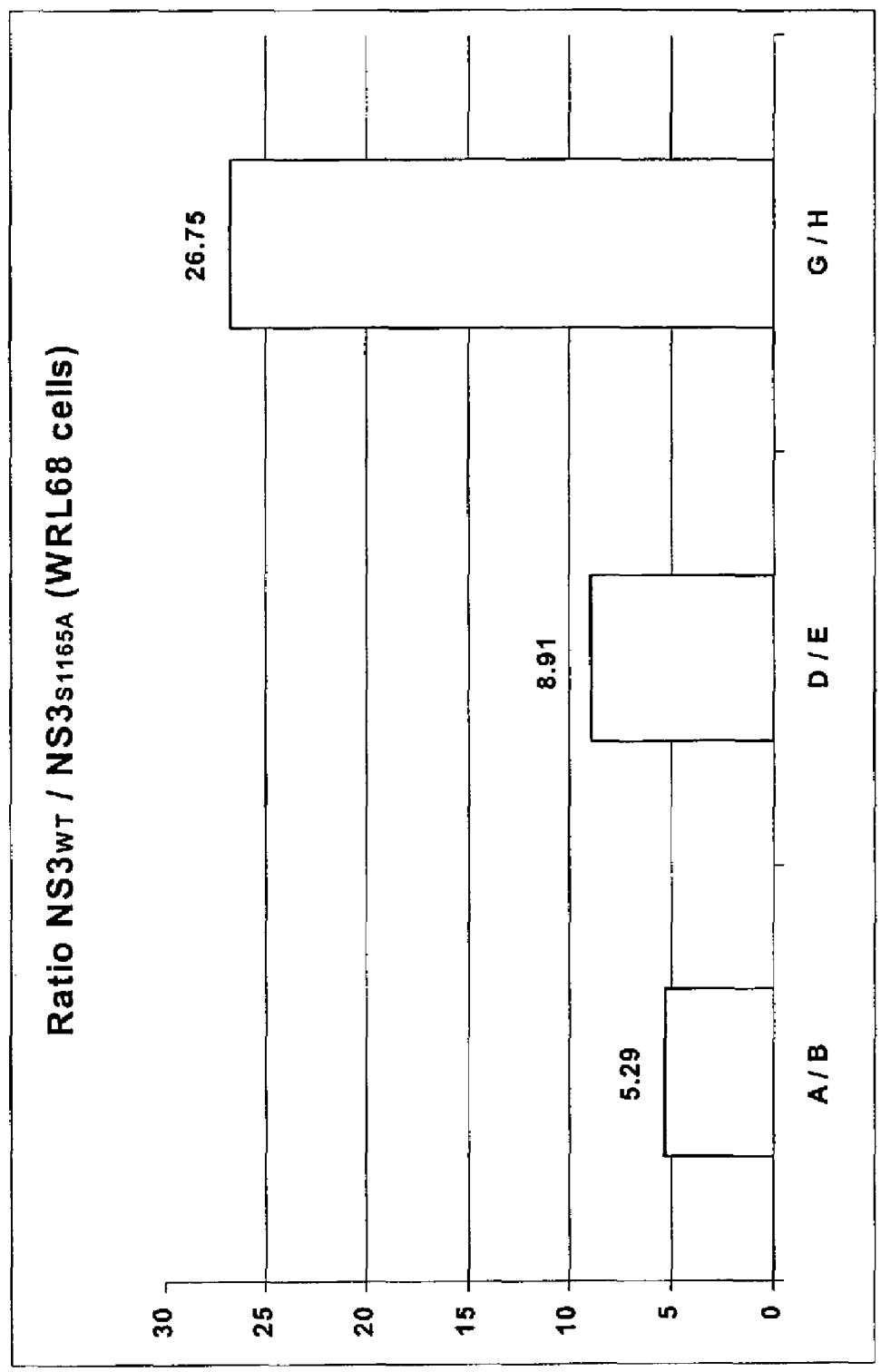

FIG. 10 shows the ratio of luciferase activity produced by constructs A, D and G with their respective active site mutants B, E and H. Luciferase assay performed on extracts of the liver cell line WRL 68 co-transfected with one of the constructs A, B, D, E, G or H, and the reporter plasmid pUHC 13-3. The luciferase activity is a measure of photon counts per second. The results show that the ratio of G/H is approximately 5 and 3.5 fold greater than the ratio of A/B and D/E, respectively. Construct G, with the longest stretch of HCV non-structural region comprising partial or full length NS3, NS4A, NS4B, NS5A and NS5B also appears to produce the greatest NS3-dependent luciferase response in the WRL68 cell line.

Figure 11:
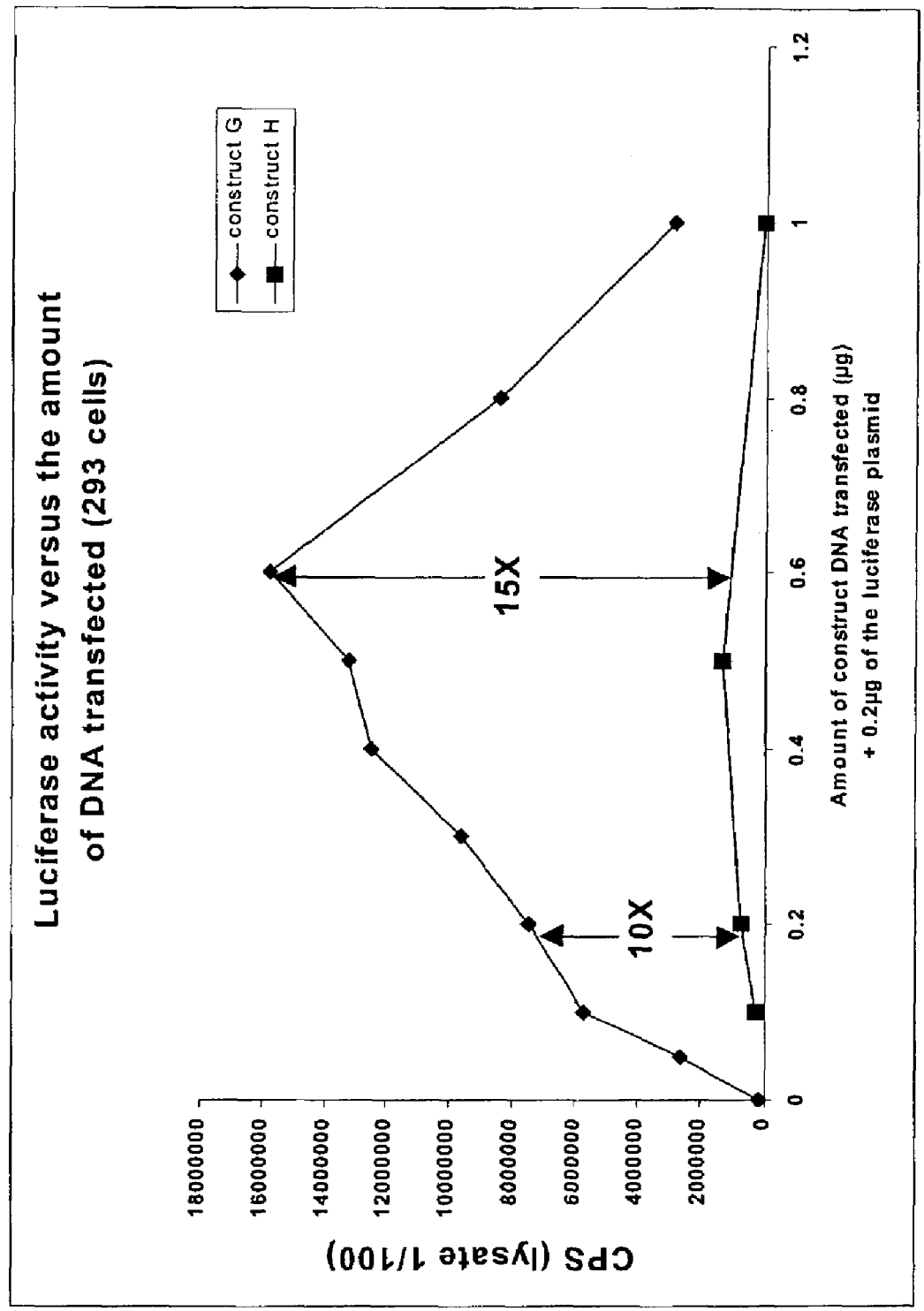

FIG. 11 shows the results of optimizing of the amount of plasmid DNA to transform the 293 cell line. Different amounts of DNA of construct G or the corresponding defective NS3 control construct H, were co-transfected with a constant amount of pUHC 13-3 (0.2 μg). Cells at 50% confluency in 6 well plates were used. The results indicate that an amount of NS3-encoding plasmid DNA approximately 3 fold greater (0.6 μg) than pUHC 13-3 (0.2 μg) produces optimal NS3-dependent luciferase signal in 293 cells.

FIG. 12 shows the results of optimizing of the amount of plasmid DNA to transform the liver cell line WRL 68. Different amounts of DNA of construct G or the corresponding defective NS3 control construct H, were co-transfected with a constant amount of pUHC 13-3 (0.21 μg). The results indicate that an amount approximately 2.5 fold greater (0.5 μg) than pUHC 13-3 (0.2 μg) produces optimal NS3-dependent luciferase signal in the liver cell line WRL 68.

FIG. 13 shows that the NS3 protein expressed from the construct I can cleave the HCV non-structural polyprotein in "trans" in 293 cells. The experiment entailed co-transfecting the pUHC13-3 reporter with one of the constructs G, H, or I. Constructs H and I were also simultaneously co-transfected along with the pUHC13-3 reporter plasmid. Transfection of only construct G with the reporter results in a strong luciferase activity signal, whereas transfection of construct H with the reporter (NS3 protease active site mutant) or construct I with the reporter (the cleavage site mutant) result in weak luciferase activity. Triple co-transfection with constructs H and I together with the reporter plasmid restores the luciferase activity signal. The functional NS3 protein expressed from construct I can process the unmodified cleavage site expressed from construct H, thereby releasing the tetracycline transactivator to initiate the expression of luciferase of the tetracycline operon. The different amounts of plasmid DNA used in the transfections are as indicated.

FIG. 14 shows the results of a similar experiment as in FIG. 13 using the liver cell line WRL68. Similarly, the results indicate that the NS3 protein produced from the construct I can cleave the HCV non-structural polyprotein in "trans" in WRL68 cell. As indicated, different amounts of plasmid DNA are used in the transfection.

FIG. 15—closed squares: show the % inhibition of HCV NS3 protease activity in tTA transactivation of SEAP expression in host cells co-transfected with construct G and pUHC13-3 reporter plasmid expressing secreted alkaline phosphatase (SEAP). Open squares: show the % inhibition of control tTA (independent of HCV NS3) activity in trans-activating SEAP in host cells co-transfected with the control pUHD15-1 and pUHC13-3 plasmids. Cells were grown post-transfection in the presence of various concentrations of the Inhibitor A. SEAP activity was measured and $EC_{50}$ and $TC_{50}$ values were determined.

DETAILED DESCRIPTION OF THE PREFERRED EMBODIMENTS

Definitions

Unless defined otherwise, the scientific and technological terms and nomenclature used herein have the same meaning as commonly understood by a person of ordinary skill to which this invention pertains. Generally, the procedures for cell culture, infection, molecular biology methods and the like are common methods used in the art. Such standard techniques can be found in reference manuals such as for example Sambrook et al. (1989) and Ausubel et al. (1994).

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission (1972).

The present description refers to a number of routinely used recombinant DNA (rDNA) technology terms. Nevertheless, definitions of selected examples of such rDNA terms are provided for clarity and consistency.

The term "recombinant DNA", "recombinant nucleic acid molecule" or "recombinant plasmid" as known in the art refers to a DNA molecule resulting from the joining of DNA segments. This is often referred to as genetic engineering.

The term "DNA segment or molecule or sequence", is used herein, to refer to molecules comprised of the deoxyribonucleotides adenine (A), guanine (G), thymine (T) and/or cytosine (C). These segments, molecules or sequences can be found in nature or synthetically derived. When read in accordance with the genetic code, these sequences can encode a linear stretch or sequence of amino acids which can be referred to as a polypeptide, protein, protein fragment and the like.

As used herein, the term "gene" is well known in the art and relates to a nucleic acid sequence defining a single protein or polypeptide. The polypeptide can be encoded by a full-length sequence or any portion of the coding sequence, so long as the functional activity of the protein is retained.

A "structural gene" defines a DNA sequence which is transcribed into RNA and translated into a protein having a specific amino acid sequence thereby giving rise to a specific polypeptide or protein. "Structural proteins" defines the HCV proteins incorporated into the virus particles namely, core "C", E1, E2, and E2-p7. "Non-structural proteins", defines the HCV proteins that are not comprised in viral particles namely, NS2, NS3, NS4A, NS5A and NS5B.

"Restriction endonuclease or restriction enzyme" is an enzyme that has the capacity to recognize a specific base sequence (usually 4, 5 or 6 base pairs in length) in a DNA molecule, and to cleave the DNA molecule at every place where this sequence appears. An example of such an enzyme is EcoRI, which recognizes the base sequence G↓AATTC and cleaves a DNA molecule at this recognition site.

"Restriction fragments" are DNA molecules produced by the digestion of DNA with a restriction endonuclease. Any given genome or DNA segment can be digested by a particular restriction endonuclease into at least two discrete molecules of restriction fragments.

"Agarose gel electrophoresis" is an analytical method for fractionating double-stranded DNA molecules based on the size of the DNA. The method is based on the fact that DNA molecules migrate through a gel as through a sieve, whereby the smallest DNA molecule has the greatest mobility and travels the farthest through the gel. The sieving characteristics of the gel retards the largest DNA molecules such that, these have the least mobility. The fractionated DNA can be visualized by staining the gel using methods well known in the art, nucleic acid hybridization or by tagging the fractionated DNA molecules with a detectable label. All these methods are well known in the art, specific methods can be found in Ausubel et al. (supra).

"Oligonucleotide or oligomer" is a molecule comprised of two or more deoxyribonucleotides or ribonucleotides, preferably more than three. The exact size of the molecule will depend on many factors, which in turn depend on the ultimate function or use of the oligonucleotide . An oligonucleotide can be derived synthetically, by cloning or by amplification.

"Sequence amplification" is a method for generating large amounts of a target sequence. In general, one or more amplification primers are annealed to a nucleic acid sequence. Using appropriate enzymes, sequences found adjacent to, or in between the primers are amplified. An amplification method used herein is the polymerase chain reaction (PCR).

"Amplification primer" refers to an oligonucleotide, capable of annealing to a DNA region adjacent to a target sequence and serving as the initiation primer for DNA synthesis under suitable conditions well known in the art. The synthesized primer extension product is complementary to the target sequence.

The term "domain" or "region" refers to a specific amino acid sequence that defines either a specific function or structure within a protein. As an example herein, is the NS3 protease domain comprised within the HCV non-structural polyprotein.

The term "reporter gene" refers to a nucleotide sequence encoding a "reporter protein". The reporter protein provides a detectable means for evaluating gene expression. The reporter gene is comprised within a "reporter plasmid". Some useful examples of reporter gene for the purpose of this invention are; secreted alkaline phosphatase (SEAP), luciferase, chloramphenicol amino transferase (CAT), β-galactosidase, green fluorescent protein (GFP), etc.

The term "reporter system", refers to the combination of two or more reporters. A non-limiting example of a reporter system useful for the purpose of the present application, is a first reporter being a genetic activator such as tTA which directs the expression of a second reporter, such as luciferase or secreted alkaline phosphatase (SEAP).

The terms "activator" and "operon" refer to a system in which an "activator" molecule binds to the operator comprised in an operon to stimulate expression of the "operon". Examples of such systems are; tetracycline transactivator (tTA), HIV-1 tat transactivator, GAL 4 transactivator, NFκβ, etc.

The term "chimeric molecule" or "chimera" as used herein refers to at least two nucleic acid domains that are not joined together in nature. Non-limiting examples of such chimeras according to the present invention include the HCV NS3-4A-4B-5A-5B-tTA domain construct. Such chimeras when expressed give rise to "fusion proteins".

The term "fusion protein" as defined herein refers to at least two polypeptidic segments that are not joined together in nature. Non-limiting examples of such "fusion proteins" according to the present invention include the parts of the HCV polyprotein co-joined with a protein having direct or indirect reporter capabilities such as tTA and SEAP.

The terms "plasmid" "vector" or "DNA construct" are commonly known in the art and refer to any genetic element, including, but not limited to, plasmid DNA, phage DNA, viral DNA and the like which can incorporate the oligonucleotide sequences, or sequences of the present invention and serve as DNA vehicle into which DNA of the present invention can be cloned. Numerous types of vectors exist and are well known in the art.

The terminology "expression vector" defines a vector as described above but designed to enable the expression of an inserted sequence following transformation or transfection into a host. The cloned gene (inserted sequence) is usually placed under the control of control element sequences such as promoter sequences. Such expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

The term "non-cytopathic" expression system defines a system that does not induce cytopathic changes in the cell system in which it is expressed. This expression system does not require co-infection with a virus and does not cause expression of non-HCV viral components that eventually could lead to cell pathology and cell death. Examples of non-cytopathic promoters are: the CMV promoter system, SV40 early-promoter system or RSV (Rous Sarcoma virus) LTR promoter system.

By "eukaryotic expression system" is meant the combination of an appropriate expression vector and a eukaryotic cell line which can be used to express a gene of interest. Plasmid vectors containing the desired gene may also be used. In all cases, the vector will contain appropriate control elements (promoter) to express gene in the cell type of interest. Eukaryotic cell types typically used are yeast (e.g. *Saccharomyces cerevisiae, Pischia pastoris*) transfected with a plasmid vector; and mammalian cells transfected with DNA vectors for transient or constitutive expression. A preferred cell line useful for the purpose of this invention is derived from liver tissue.

A host cell or indicator cell has been "transfected" by exogenous or heterologous DNA (e.g. a DNA construct) when such DNA has been introduced inside the cell. The transfecting DNA may or may not be integrated (covalently linked) into chromosomal DNA making up the genome of the cell. In prokaryotes, yeast, and mammalian cells for example, the transfecting/transforming DNA may be maintained on an episomal element such as a plasmid. With respect to eukaryotic cells, an example of a stably transfected cell is one in which the transfecting DNA has become integrated into a chromosome and is inherited by daughter cells through chromosome replication. This stability is demonstrated by the ability of the eukaryotic cell to establish cell lines or clones comprised of a population of daughter cells containing the transfecting DNA. Transfection methods are well known in the art (Sambrook et al., 1989; Ausubel et al., 1994).

The nucleotide sequences and polypeptides useful to practice the invention include without being limited thereto, mutants, homologs, subtypes, quasi-species, alleles, and the like. It is understood that generally, the sequences of the present invention encode a polyprotein. It will be clear to a person skilled in the art that the polyprotein of the present invention and any variant, derivative or fragment thereof, is auto-processed to an active protease.

As used herein, the designation "variant" denotes in the context of this invention a sequence whether a nucleic acid or amino acid, a molecule that retains a biological activity (either functional or structural) that is substantially similar to that of the original sequence. This variant may be from the same or different species and may be a natural variant or be prepared synthetically. Such variants include amino acid sequences having substitutions, deletions, or additions of one or more amino acids, provided the biological activity of the protein is conserved. The same applies to variants of nucleic acid sequences which can have substitutions, deletions, or additions of one or more nucleotides, provided that the biological activity of the sequence is generally maintained.

The term "derivative" is intended to include any of the above described variants when comprising additional chemical moiety not normally a part of these molecules. These chemical moieties can have varying purposes including, improving a molecule's solubility, absorption, biological half life, decreasing toxicity and eliminating or decreasing undesirable side effects. Furthermore, these moieties can be used for the purpose of labeling, binding, or they may be comprised in fusion product(s). Different moieties capable of mediating the above described effects can be found in *Remington's The Science and Practice of Pharmacy* (1995).

Methodologies for coupling such moieties to a molecule are well known in the art.

The term "fragment" refers to any segment of an identified DNA, RNA or amino acid sequence and/or any segment of any of the variants or derivatives described herein above that substantially retains its biological activity (functional or structural) as required by the present invention.

The terms "variant", "derivative", and "fragment" of the present invention refer herein to proteins or nucleic acid molecules which can be isolated/purified, synthesized chemically or produced through recombinant DNA technology. All these methods are well known in the art. As exemplified herein below, the nucleotide sequences and polypeptides used in the present invention can be modified, for example by in vitro mutagenesis.

For example, as defined in the present invention, a desired fragment of NS3 protein must retain its protease activity. A desired fragment of the NS4A protein would retain its protease co-factor activity (functional activity) and also retains its hydrophobic portion that allow embedding in the ER membrane (structural activity). A desired fragment of the NS4B protein would retain its structural activity inasmuch as it would allow polyprotein processing as close as possible to the native one. A desired fragment of the NS5A protein would retain its structural activity to allow polyprotein processing as close as possible to the native one while also retaining its functional activity to provide a functional NS5A/5B cleavage site. A desired fragment of the NS5B protein would have to be sufficient to retain a functional NS5A/5B cleavage site. For example, the first 6 amino acid of the NS5B protein are sufficient for this purpose. Such functional or structural activity for each respective domain may easily be assessed by the person skilled in the art without undue experimentation.

The term "cleavage site" as used herein refers to a polypeptide capable of being cleaved in "cis" or in "trans" by the HCV NS3 protease.

The term "target cleavage site" or "target site" as used herein refers to a cleavage site downstream on the NS3/4A cleavage site. At least one target site of the NS3 protease must be cleaved in order to obtain translocation of the transactivator, expression of the reporter gene and achieve measurement of the reporter gene product. The NS3/4A cleavage site is not considered herein a "target" site because its cleavage by itself will not release the reporter gene product.

The term "functional cleavage site" as used herein means a cleavage site of the precursor polypeptide that has been modified (by mutation or any other chemical means) but still remains cleavable by the NS3 protease. Non-limiting examples of such modification include conservative substitution of nucleic acid codon or amino acid.

Preferred Embodiments

Cell-Based Assay

Therefore, in accordance with a first embodiment of the present invention, there is provided a surrogate cell-based system to evaluate the protease activity of Hepatitis C virus NS3 protease comprising:

a) a first chimeric DNA molecule comprising:
 i) a non-cytopathic expression system capable of inducing expression of said first chimera upon transfection in a mammalian cell; and
 ii) a HCV recombinant DNA molecule operably linked to said expression system; said HCV DNA molecule encoding the NS3–5 polyprotein comprising:
  an active NS3 protease domain,
  a NS4A domain sufficient to allow embedding in the ER membrane upon translation and acting as co-factor for the NS3 protease activity,
  NS4B and NS5A domains, including any derivative, variant or fragment thereof, and
  NS5B protein including any derivative, variant or fragment thereof, sufficient to provide a NS5A/5B cleavage site for said NS3 protease;
 iii) and a transactivator domain fused downstream of said HCV DNA molecule, said transactivator domain encoding a transactivator molecule capable of initiating expression of a reporter gene;
b) and a second chimeric DNA molecule encoding said reporter gene co-joined to an operon responding to said transactivator molecule;

whereby expression of said first recombinant molecule leads to the production of a fusion polyprotein anchored to the endoplasmic reticulum of said mammalian cell, said anchored protein capable of being cleaved by said protease thereby allowing translocation of said transactivator domain for inducing expression of said reporter gene as a means to evaluate said protease activity.

In a preferred aspect of the first embodiment, the chimeric molecule encompasses a nucleotide sequence capable of expressing the HCV polyprotein having the NS3 domain, variants, derivatives or fragments thereof sufficient to provide an active protease once translated. This comprises a NS3 protein truncated to exclude the helicase domain, or an NS3 protein where the helicase domain is inactivated.

The NS4A domain necessary for the present invention requires that the translated NS4A protein, variants, derivatives or fragments thereof, be sufficient to allow embedding of the polyprotein in the ER membrane upon translation and act as co-factor for the NS3 protease activity.

The NS4B domain necessary for the present invention requires that the translated protein be of sufficient length to allow correct structural orientation of the NS3 protease in view of the NS5A/5B target cleavage site. Variants, derivatives or fragments of the NS4B protein can therefor be mutated in its cleavage sites (4A/4B or 4B/5A), or mutated to eliminate its native biological activity without compromising its orienting effect on the polyprotein.

The NS5A domain necessary for the present invention requires that the translated protein be of sufficient length to allow correct structural orientation of the NS3 protease in view of the NS5A/5B target cleavage site. Variants, derivatives or fragments of the NS5A protein can therefor be mutated in its upstream cleavage site (4B/5A), or mutated to eliminate their respective biological activity without compromising its orienting effect on the polyprotein and the NS5A/5B cleavage site.

Finally, the NS5A/5B cleavage site necessary for the present must be functional i.e. recognized and cleaved by the NS3 protease. Such functional target cleavage site include derivatives, variants or fragments thereof so long as it is capable of being cleaved by the NS3 protease. A preferred embodiment of the NS5A/5B cleavage site encompasses that first six amino acids of the NS5B domain.

In an alternative aspect of this first embodiment, there is provided the nucleotide sequence coding for the full length NS3 polyprotein. Alternatively, there is provided a partial nucleotide sequence coding for a partial polyprotein comprising variants of the necessary domains as defined above. Alternatively, the chimeric molecule encompasses nucleotide sequence capable of expressing derivative, variant or fragment of the precursor polyprotein comprising all functional cleavage sites: NS3/4A; 4A/4B; 4B/5A; and 5A/5B. Alternatively, at least the NS5A/5B is a functional cleavage site whereas the other cleavage sites may have been modified to become non-functional.

In accordance with a specific aspect of this first embodiment, the non-cytopathic promoter system comprises the CMV promoter, the SV40 early-promoter system or the RSV (Rous Sarcoma virus) LTR promoter system.

In accordance with a specific aspect of this first embodiment, the reporter system comprises a trans-activator domain joined to the first recombinant nucleic acid molecule whereby the transactivator, when cleaved from the expressed fusion protein, migrates to the nucleus to, in turn, activate the expression of a reporter gene of which the product can be measured as a means for evaluating NS3 protease activity. The fusion of a transactivator domain provides an amplification level to increase the sensitivity of the assay. In accordance with this particular aspect, the activation of the reporter gene system by the transactivator may be specifically inhibited as a means to ensure that cleavage of the precursor polyprotein is specific (built-in negative control). One such particular aspect comprises a system adapted from the method of Gossen, M. and Bujard, H. (1992), which describes the design and potential use of a tetracycline controlled transactivator in a mammalian cell line. In this method, the tet repressor is fused to the activation domain of the herpes simplex virus protein 16 (VP16) thereby generating a tetracycline dependent transactivator (tTA). This tTA initiates the transcription/expression of a reporter gene under the control of a combined tet operon/viral promoter. The product of the reporter gene is an indication of gene activation and protein expression.

Still, in a preferred aspect of the reporter system, the trans-activator may be located anywhere on the chimeric molecule or fusion protein, as long as it is downstream from the target cleavage sites and is therefore released upon cleavage. More preferably, the trans-activator is located at the 3'-end of the recombinant molecule.

Non-limiting examples of trans-activator include tetracycline trans-activator (tTA), NFκB, HIV-1 tat and GAL-4. More preferably, the trans-activator is tTA.

Non-limiting examples of reporter molecule include: secreted alkaline phosphatase, β-galactosidase, luciferase, chloramphenicol aminotransferase and green fluorescent protein. Preferably, the reporter molecule is SEAP or luciferase. More preferably, the reporter molecule is SEAP.

In a preferred aspect the reporter system is a combination of tTA and luciferase; or a combination of tTA and SEAP. More preferably, the reporter system is a combination of tTA and SEAP.

It is an aspect of the present invention that different permutations of a trans-activator and a reporter system can be combined using methodologies well known in the art, all these are within the scope of this invention.

Since there are different reporter molecules useful for the purpose of this invention, the detection of the reporter gene product corresponds accordingly with the use of known methods. For example; luciferase can be measured by a chemiluminescent reaction using Co-enzyme A as a luciferase substrate (Luciferase Assay System from Promega, NI, USA) and SEAP can be measured by a chemiluminescent reaction incorporating CSPD substrate and an enhancer (Tropix, Inc., MA, USA).

Recombinant DNA Molecules and Proteins

In a second embodiment, the invention encompasses the recombinant DNA molecules useful in this assay and any fragment, variant and derivative thereof.

In accordance with a specific aspect of this second embodiment of this invention, there is provided a nucleic acid molecule as defined in SEQ ID NO. 1.

In a third embodiment, the invention encompasses recombinant proteins produced from the recombinant DNA molecules of the invention.

In accordance with a specific aspect of this second embodiment, there is provided an amino acid sequence as defined in SEQ ID NO. 2.

In accordance with the above stated embodiment of the amino acid and nucleotide sequence, all variants, derivatives and fragments thereof being functionally equivalent to the sequences herein are within the scope of this invention.

Vectors

In a fourth embodiment, the invention also encompasses vectors comprising any of those recombinant DNA molecules. It is a particular aspect of this fourth embodiment that the nucleic acid molecule of SEQ ID NO. 1 can be inserted into an expression plasmid for transfection into a host mammalian cell. In a preferred aspect of the fourth embodiment, different plasmids, vectors or viruses useful for the purpose of this invention include mammalian expression plasmids, vectors or viruses that are able to transform a mammalian host cell stably or transiently. These are well known and are within the scope of this invention. More preferably, the plasmids are selected from the group consisting of: the pUHD15-1 CMV promoter-based plasmid harboring the tTA gene and the pUHC13-3 tTA controllable luciferase or SEAP reporter plasmid. In a most preferred aspect of this fourth embodiment, the nucleic acid of SEQ. ID NO. 1 is inserted in pUHD15-1 plasmid.

Transfection

Transfection of the above-mentioned vectors in host cells may be carried out simultaneously (co-transfection) or sequentially. As an alternative, the transfection of the reporter system may be carried out first, in order to obtain stable transfectants, that are later used for a second transfection of the HCV domain-containing vector to obtain double transfectants (transient or stable) useful for the present invention.

Host Cells

In a fifth embodiment, the present encompasses eukaryotic host cells transfected with these vectors. Therefore, in accordance with a specific aspect of this fifth embodiment, there is provided a host cell transfected with an expression plasmid comprising the chimeric molecule as defined above. More particularly, there is provided a mammalian cell line transfected with the nucleic acid molecule of SEQ ID NO. 1. In a preferred aspect of the fifth embodiment, the host cell is a mammalian cell that is transformed stably or transiently. Non-limiting examples of mammalian host cells and cell lines include primary hepatocytes, liver cell lines, fibroblasts, lymphocytes, kidney cells, etc. More preferably, there is provided a human cell line transiently transfected with the chimeric molecule. Even more preferably, the human cell line is a liver or kidney cell line. Most preferably, the host cell may be selected from the group consisting of: 293, Huh-7, WRL68, HepG2, and Chang cells.

Method for Identifying Inhibitors

In a sixth embodiment, the invention encompasses a method for evaluating NS3 protease activity by using the recombinant molecules and transfected host cells of the invention. In a particular aspect of this sixth embodiment, there is provided a method for screening for anti-HCV inhibitor by using the system as defined above.

In accordance with a specific aspect of this sixth embodiment, there is provided a method for assaying HCV NS3 protease activity, comprising the steps of:
  a) firstly incubating transfected host cells as described above under conditions which cause HCV NS3–5 polyprotein and said reporter gene product to be expressed; and
  b) measuring the amount of said gene product expressed.

In accordance with a further specific aspect of this sixth embodiment, there is provided a method for identifying a compound as inhibitor of the HCV NS3 protease comprising the steps of:
  a, b) assaying the activity of said protease in the absence of said compound by the method as defined above; and
  c) assaying the activity of said protease in the presence of said compound by the method as described above, wherein said compound is added to the host cells after said first incubation, and host cells further incubated before assaying said activity; and
  d) comparing the results of step c) with the results of step b).

The assays and methods of the present invention are conducted under conditions for mammalian cell growth that are well known to a person skilled in the art, i.e., physiological pH, salt concentrations using buffers such as PBS, temperatures between 30° to 42°, appropriate cell culture media and providing sufficient time for cell growth.

In a preferred aspect of the method of this invention, the transfected host cells are incubated for a sufficient time to allow the expression and processing of the encoded precursor amino acid sequence and for the expression of the reporter molecule. More specifically the cells are incubated for at least one hour and most specifically for at least 18 h, and the amount of reporter gene product compared to a standard. Herein, a standard refers to, either host cells that have not been transfected or host cells transfected with a vehicle (a vector or plasmid not carrying the recombinant nucleic acid molecule encoding the precursor amino acid sequence). In a preferred aspect of the fifth embodiment, the transfected host cells are further incubated in the presence or absence of a test compound(s) for about 30 h, more particularly for about 20 h and most particularly for about 10 h, and the amount of reporter gene product compared.

EXAMPLES

Materials

All restriction enzymes were purchased from Pharmacia Biotech Inc. (Quebec, Canada). Polymerase chain reactions were performed with ID-proof polymerase obtained from ID Labs (ON, Canada) using manufacturer instructions. Thermostable alkaline phosphatase was obtained from Gibco-BRL (MD, USA). Ligation reactions were performed using T4 DNA ligase obtained from Pharmacia Biotech Inc. (Quebec, Canada) following the manufacturer's instructions. The HCV-tTA chimeras were constructed using the vector pUHD15-1 which encodes the tTA gene expressed by the CMV promoter (Display Systems Biotechnology, Inc., CA, USA), the nucleotide sequence encoding HCV proteins inserted using the restriction sites Xba 1. The luciferase reporter plasmid, pUHC13-3 was also obtained from Display Systems Biotechnology. Plasmid pCR3.1 was obtained from Invitrogen and the recombinant vaccinia virus expressing the T7 RNA polymerase was obtained from Bernard Moss (NIH, MD, USA). The HCV 1b viral cDNA was generated by RT-PCR of a human serum sample infected with the virus using primers derived from HCV 1b sequence of HCV J4/83 (Genebank accession number: D13558) and primers used for the amplification of the 3' end were derived from Genebank accession number D36922. This HCV cDNA was sequenced (partial sequence in SEQ ID NO 1) and served as a template in the amplification reactions of the specific HCV segments used in constructing the recombinant molecules shown in FIGS. 2A to 2I.

Standard methods were employed for all amplification reactions, restriction enzyme digestion, site-directed oligonucleotide mutagenesis, cloning, isolation of plasmid DNA, cell culture, transfections and western blotting analyses (Sambrook et al., 1989). Amplification products generated with the primer pairs described hereinabove were digested with the restriction enzymes Nhe 1 and Xba 1, and cloned into the Xba 1 restricted plasmid pUHD15-1, transformed into E. coli. The transformants were screened for directionality by restriction enzyme analysis. The selected in-frame HCV-tTA chimeras are shown in FIGS. 2A to 2I. Each of these HCV-tTA chimeras were additionally subcloned into the plasmid pCR3.1 by TA cloning (Invitrogen, CA, USA) thereby placing the HCV-tTA chimeras under the control of a T7 promoter.

Example 1

RT-PCR of HCV 1B and Sequencing of Amplified Product

Human serum sample carrying the HCV 1b RNA was reverse transcribed and amplified using 12 sense and antisense primers spanning HCV 1b cDNA sequence (HCV J4/83; accession number D13558). The 3'-end sequence was amplified using primers derived from the HCV accession number D63922) described by Kolykhalov et al. (1996). RT-PCR reactions generated 4 overlapping fragments covering the entire HCV-1b. The fragments were assembled through digestion at unique restriction enzyme sites and ligated forming the full length HCV cDNA. This resulting cDNA was sequenced in its entirety and used as a template in all amplification reactions, the amplification products were used in the construction of the chimeras described in this application. The sequenced polyprotein region fused to the tTA is shown in SEQ ID NO 1 and the translated amino acid sequence in SEQ ID NO.2.

Example 2

Amplification of the HCV Fragments Used in Constructing the Chimeras

The forward primer, GGCGCTAGCGCGCCCATCACG-GCCTAC (SEQ ID NO 3) complementary to the 5'-end of the NS3 gene contains an Nhe 1 site was used in all the amplification reactions. All the reverse primers complementary to the 3'-end, used herein contain an Xba 1 site. The reverse primer GGCTCTAGAGTAAGGGAGGTGT GAGGC (SEQ ID NO 4) was used to amplify the sequences for chimeras A and B and includes the NS4B P1' to P6' cleavage site. The reverse primer GGCTCTAGAGTAAGG-GAGGTGTGAGGGGCGCTCTTCC (SEQ ID NO 5) was used to amplify the HCV sequence for chimera C and corresponds to the NS4B P1' to P6' cleavage site in which substitutions in the NS4A/NS4B P1–P1' residues are introduced.

The two overlapping reverse primers, GCAGCAGAC-GACGTCCTCGAATTCCCGGTAG AG GAC (SEQ ID NO 6) and GGCTCTAGACCATGTGTAGGACATCGAG-CAGCAGACGACGTCCTC (SEQ ID NO 7) were used to amplify the HCV sequences for chimeras D and E, in which the NS4A/NS4B cleavage site of the respective clones A and B is replaced with the NS5A/NS5B cleavage site.

Two overlapping reverse primers, GCAGCAGAC-GACGTCCTCGAATTCCCGGTAGAGGAC (SEQ ID NO 6) and GGCTCTAGACCATGTGTAGGACATAGGC-CTGCAGACGACGTCCTC (SEQ ID NO 8) were used to amplify the HCV sequence for chimera F and corresponds to the NS5B P1' to P6' cleavage site in which substitutions in the NS5A/NS5B P1–P1' residues are introduced.

The HCV sequence for chimera G was generated by amplifying the full length HCV cDNA with the primers of SEQ ID NO 3 and SEQ ID NO 7. This produced a sequence spanning the HCV NS3 to NS5B-P6' codon, inclusively.

Similarly, the HCV sequence for chimera I was generated by amplifying the full length HCV cDNA template with the primers of SEQ ID NO 3 and SEQ ID NO 8. This produced a sequence spanning the HCV NS3 to NS5B-P6' codon, inclusively and contains a P1–P1' cleavage site substitution.

Clones B, E, and H were amplified using an HCV cDNA template modified by site-directed mutagenesis with the oligonucleotide CCCCCGGGTGCACACAGCTGCCC GGAAGATGCCCACAACGGC-CCCGAAGGGCAGAGCAGTGGGCCACCCG-CAGAGCC (SEQ ID NO 9) which introduces a serine to alanine mutation at residue 1165, producing an NS3 active site mutant.

The non-structural regions of the HCV polyprotein included in the constructs A to I, these are processed by NS3 protease cleavage in which specificity is determined by the amino acid sequence spanning the junctions of each of the proteins. This cleavage site preference was previously reproduced in vitro with peptide substrates and purified NS3 protease (reviewed in Kwong et al., 1998).

In the present application in vivo cleavage is examined. Expression of the polyprotein in a variety of heterologous expression systems and the appearance of mature HCV proteins is monitored through an indirect examination of the processed products by western blot analyses. In an effort to provide optimal high through-put reporter-based assay for NS3 protease activity, different constructs of HCV polyprotein segments fused to an activator/reporter shown in FIGS. 2A to 2I were evaluated.

Three different families of HCV-tTA fusions were constructed and the efficiency of in vivo cleavage examined. The results demonstrate that the efficacy of NS3 cleavage is not only determined by the sequence spanning the cleavage site but also by the positional context of the site with respect to other portions or domains in the HCV polyprotein.

The three families of HCV-tTA fusions that are used to demonstrate this finding are:

clones A, B, and C that span NS3 to NS4A have the tTA activator fused to the 6th amino acid of NS4B such that cleavage of the tTA mimics the processing of NS4B protein;

clones D, E, and F are similar to (i) except that the 12 amino acid segment spanning the NS4A/NS4B junction (DEMEEC↓ASHLPY, corresponding to amino acids 683 to 694 of SEQ ID NO 2) was changed to the sequence spanning the NS5A/NS5B junction (EDVVCC↓SMSYTW, corresponding to amino acids 1391 to 1402 of SEQ ID NO 2), this variant positions the tTA in the NS4B context yet harbors a more efficient cleavage site (NS5A/NS5B); and clones G, H, and I include the HCV non-structural region that begin at the NS3 amino-terminus and terminates at the sixth amino acid of NS5B, fused to the tTA such that cleavage of the tTA mimics processing of the NS5B protein in its positional context.

Variants (clones B, E, and H), contain a NS3 protease active site mutation (serine 1165 to alanine, the amino acid residue is at the 1165th position from the start of the HCV polyprotein), these are used as controls to demonstrate that tTA cleavage is dependent on an active NS3 protease.

Variants (clones C, F, I), contain the P1–P1' cleavage site mutated to an R-P di-amino acid motif, these are used as controls to demonstrate that tTA processing is exclusively dependent on a functional NS3 cleavage sequence site at the engineered junction with the tTA activator.

Example 3

Visualization of HCV-tTa Fusions in Transfected/T7 Vaccinia Virus (vvT7-3) Infected Cells Since the expression of the HCV NS3 protease with the CMV promoter was too low for visualization by Western analysis, we verified the activity of the protease in each of the chimeras by the expression of the fusion proteins in 293 cells using the vaccinia virus T7 (vvT7-3) expression system (Elroy-Stein, O. and Moss, B., 1998).

Cells grown to 60% confluency in 6 well plates in DMEM-10% FBS were infected with vvT7-3 (moi 10–15) and transfected with 5 μg of pCR3.1 HCV-tTA constructs A, B and C using the calcium phosphate method. Eighteen hours post-transfection, the cells were harvested and proteins from whole cell lysate resolved by SDS-PAGE, electrophoretically transferred to a membrane and the membrane probed with HCV specific polyclonal antibodies.

Plasmid pCR3.1 containing chimeras A, B, C, D, E, F, G, H or I were transfected into the vvT7 infected 293 cells and the HCV protein processing examined by Western blot analysis using HCV specific polyclonal anti-serum. Chimera A is shown to produce mature NS3 and NS4A protein reactive bands (FIGS. 3A and 3B, lanes A, respectively). As the NS4A protein comprises only 54 amino acids, it was necessary to run a gel under conditions that allow the detection of a small molecular weight molecule (FIG. 3B bottom panel). Chimera B, which encodes the inactive S1165A mutation of NS3, does not process the polyprotein precursor as shown by the absence of NS3 and NS4A reactive bands (FIGS. 3A and 3B, lanes B, respectively). Chimera C, having a NS4A/NS4B cleavage site mutation, produces a reactive band corresponding to mature NS3 (FIG. 3A, lanes C) but no mature NS4A reactive band. The lack of cleavage at the NS4A-tTA cleavage site (FIG. 3B, lanes C) is confirmed by the detection of the NS4A-tTa fusion in the anti-NS4A western blot.

In chimeras D, E and F, the NS4A/4B cleavage site was replaced with the NS5A/5B cleavage site. Expression of the transfected host cells containing chimera D produce a reactive band corresponding to mature NS3 protein (FIG. 4, lanes D). Chimera E, carrying the S1165A mutation has no apparent NS3 reactive band (FIG. 4, lanes E), demonstrating that the polyprotein precursor is not processed. Chimera F, having an active NS3 protease, produces a mature NS3 but has a cleavage site mutation that presumably blocks cleavage at the NS4A-tTA cleavage site (FIG. 4, lanes F).

The anti-NS4A antiserum available, recognizes an epitope at the C-terminal of NS4A protein. Chimeras D, E and F have had this segment modified to provide the NS5A/NS5B cleavage site. Therefore, western blot analyses using anti-NS4A anti-serum as a probe for these chimeras could not detect the modified NS4A.

Chimeras G, H and I, contain most of the HCV polyprotein. Expression of the transfectants containing chimera G resulted in the precursor polyprotein processed to the expected mature proteins, NS3, NS4A, and NS5A. These were visualized by western analyses probed with the respective anti-sera (FIGS. 5A, 5B, and 5C, lanes G, respectively). Chimera H, carrying the S1165A mutation, inactivating NS3, does not process the polyprotein precursor and fails to produce any of the mature proteins (FIGS. 5, lanes H). Chimera I, carrying a NS5A/5B cleavage site mutation, produces a mature NS3 and NS4A proteins (FIGS. 5A and 5B, lanes I) and fails to cleave at the NS5A/tTA cleavage site (FIG. 5C, lanes I).

Example 4

Luciferase Assay

The three families (clones A, D, and G) of HCV-tTA chimeras, and their active site and cleavage site mutant variants, were each co-transfected with the pUHC13-3 reporter into 293 cells to determine the extent of NS3-dependent luciferase expression (FIG. 6). Cells in 35 mm wells were co-transfected with each of the constructs described in FIGS. 2A to 2I and the pUHC13-3 reporter plasmid using the calcium phosphate method. The cells were harvested 48 hours post-transfection and washed twice in phosphate buffered saline. The harvested cells were lysed in 200 μl of lysis buffer (25 mM Tris-phosphate pH7.8, 2 mM DTT, 2 mM 1.2 diaminocyclohexane-N,N,N',N'-tetraacetic acid, 10% glycerol and 1% Triton X-100) and centrifuged for 5 min at 12 000 g. An aliquot of 10 μl of supernatant was mixed with 50 μl of the luciferase assay reagent (Promega) in a 96 well plate and the amount of light produced measured using a Digene luminometer or Packard top-count scintillation counter.

Chimera A produced ~1 200 000 cps of luciferase activity, this signal is 2-3 fold higher than the luciferase (500 000 cps) produced by chimera B (inactive NS3 protease) and chimera C (cleavage site mutation).

The HCV-tTA fusion family represented by chimera D produced ~1 300 000 cps of luciferase activity in 293 cells. The NS3 dependence of this signal is highlighted by the significantly lower amount of luciferase (100 000–300 000 cps) produced by chimera E (inactive NS3 protease) and chimera F (cleavage site mutation).

The longest HCV-tTA fusion represented by chimera G produced the highest luciferase signal (~2 200 000 cps). The NS3 dependence of this signal is reinforced by the low amount of luciferase (100 000–300 000 cps) produced by chimeras H (inactive NS3 protease) and chimera I (cleavage site mutation).

The NS3 dependent luciferase signal produced in transfected 293 cells can be expressed as a ratio of the signal obtained from wild type/active site mutant (FIG. 7).

The ratio of A/B, D/E and G/H produce a 3, 15.4 and 28.1 fold activation of luciferase, respectively.

These results show that construct G having all domains of the HCV NS3–5 polyprotein (including the region from NS3 up to the sixth amino acid of NS5B) containing the NS5A/NS5B cleavage site preceded by its "natural" context, produced the highest activation of luciferase.

Example 5

Tetracycline Internal Control Validation

Mature tTA expressed from the HCV-tTA chimeras function in a tetracycline controllable fashion. For example FIG. 8, demonstrates that lysates from cells co-transfected with the chimera G expressed from the pUD15-1 and the pUHC13-3 reporter show tetracycline sensitive luciferase activity. Cells expressing chimera G in the absence of tetracycline produce over 2,000,000 cps of luciferase activity. In the presence of tetracycline, the activity of the mature tTA activator is inhibited resulting in 40000 cps of luciferase activity. In the absence of tetracycline, the amount of luciferase produced by the G chimera transfectants, is the same order of magnitude as the amount of luciferase produced from control pUHD15-1. Moreover, co-transfection of chimera H and pUHC13-3 demonstrates that tTA activation of luciferase requires an active NS3 protease. Chimera H transfectants encoding an inactive protease fail to produce mature tTA, resulting in only 90 000 cps luciferase activity.

Example 6

Luciferase Assay in Transfected Liver Cells (WRL68)

Since HCV is found in liver cells it was important to verify that this assay works equally well in liver cells. Therefore, luciferase activation was examined in the liver cell line WRL68 for each of the chimeras (FIG. 9). Activation in this cell line was found to be NS3-dependent and efficiency in activating luciferase expression in the different chimeras (FIG. 10) is analogous to the activation efficiency of the chimeras in 293 cells.

Example 7

Optimizing Luciferase Activation Relative to the Amount of DNA

A critical aspect of co-transfection experiments is the amount of plasmid DNA introduced into cells. This two component system required optimization of the relative amounts of the HCV-tTA plasmid and luciferase reporter plasmid. A range, from 0.1 to 1 μg, of HCV-tTA plasmid G was co-transfected into 293 cells (at 50% confluency in 6 well plates) with 0.2 μg of the pUHC13-3 luciferase reporter plasmid (FIG. 11). Optimal luciferase activation in these transfectants was achieved with 0.4 to 0.7 μg of HCV-tTA plasmid. Similarly, optimal luciferase activation was seen with 0.4 to 0.7 μg of HCV-tTA chimera G in WRL68 cells (FIG. 12).

Example 8

NS3 Trans-Cleavage Activity

NS3 protease produced from the full length polyprotein can cleave the NS5A/5B junction in trans (Tomei et al., 1993; Bartenschlager et al., 1994; Lin et al., 1994). The utility of HCV-tTA chimeras were used to demonstrate NS3 trans cleavage activity. FIG. 13 reveals that chimera G can activate the expression of luciferase to generate ~2 000 000 cps. Chimera H and I which contain an inactive protease and a cleavage site mutation at the tTA junction, respectively, activate significantly less luciferase (see FIG. 5). A triple transfection of chimera H, I and the pUHC13-3 reporter into 293 cells restores luciferase activity (~2 000 000 cps) demonstrating that the active NS3 protease expressed from chimera I can cleave the "native" (unmodified) NS5A/5B junction encoded in chimera H. A similar triple transfection of liver cell line WRL68 partially restored luciferase activity (FIG. 14).

Example 9

SEAP Assay (High-Throughput System)

Liver cells, Huh-7 grown in CHO-SFMII media (GIBCO BRL) supplemented with 10% fetal calf serum were co-transfected with chimera G and a pUHC13-3 SEAP (modified pUHC 13-3) reporter plasmid using FuGene6 Boehringer Mannheim (Mannheim, Germany). The pUHC 13-3 reporter plasmid was modified by replacing luciferase with SEAP. Following a 5 h incubation, the cells were washed, trypsinized and plated at 80 000 cells per well in a 96 well culture plate containing different concentrations of the compound, and incubated for 24 h. The amount of SEAP secreted into the media was measured with the Phospha-light substrate (Tropix Inc., MA, USA).

Example 10

Validation with a Specific NS3 Inhibitor BILN 1924

The assay described herein was validated with a compound shown to inhibit NS3 protease at an $IC_{50}$ of 40 nM by the enzymatic assay described in WO 00/09543 incorporated herein by reference.

FIG. 15 shows that the amount of measured SEAP secreted is reduced in a dose dependent manner. This result further shows that this compound is cell-permeable and retains its inhibitory efficacy in a cell-based assay. The $EC_{50}$ of this compound as determined in the assay of the present invention is 75 nM. Increasing the concentration of the compound resulted in a dose dependent decrease in the amount of SEAP secreted, corresponding to an increased inhibition in the cleavage at one or more site(s) by NS3 protease activity. Moreover, in the control experiment (FIG. 15, open squares) the compound did not significantly inhibit the control tTA activity at concentrations below 1 μM. This compound validates the utility and specificity of the assay of the present invention.

It is a surprising and advantageous outcome of this invention, that the HCV chimeric molecule encompassing all the cleavage sites of the native NS3 polyprotein up to about the 6th amino acid of NS5B is the most effective construct for the purpose of evaluating HCV NS3 protease activity in a mammalian cell. This chimera mimics the processing of the full length HCV non-structural region forming the NS3–NS4A protease heterodimer complex thereby improving the activity of NS3 protease activity. The improved effectiveness of this recombinant molecule has provided the basis for a new system for assaying NS3 protease activity that is more specific and sensitive than other known assays. Further, this improved new system is useful in establishing an assay system to screen for inhibitors of protease activity that can be scaled up to a high-throughput screening system.

Discussion

As will be seen in FIGS. 7 and 8, Applicant has reproduced representative constructs of the prior art (construct A and D) and has tried without optimal results to use this system in a high throughput assay. The signal obtained and the signal/noise ratio were non-optimal to allow for automation of the assay.

One way to improve the sensitivity of the assay has been to provide a construct that substantially reproduces the authentic conformation of the mature NS3–5 polyprotein, thereby mimicking the NS3 protease activity in its native context. Surprisingly, compared to systems of the prior art, the construct of the present invention provides an increase in the signal/noise ratio from 2× to 6× higher.

The Applicant has therefore developed a new and improved cell-based system and assay for measuring the protease activity in a reliable and reproducible manner. After carrying out the experiments of FIGS. 7 and 9, Applicant found with surprise that additional cleavage sites on the protease substrate improves the signal obtained. This is surprising inasmuch as only one transactivator molecule is released whether the substrate is cleaved once, twice or at three places. The fact that the signal increases is unexpected and favorable to this system. More specifically, FIGS. 7 and 9 show the increase in signal obtained when using construct A (1 cleavage site, described in the prior art) vs construct D (one more cleavage site) vs construct G (native polyprotein). Applicant could not have predicted that construct G would have provided an increase in activity sufficiently high and reproducible enough to set-up a high-throughput assay.

FIGS. 8 and 10 show that depending on the cell line used, each additional cleavage site provides between two to 6 times more signal without increasing the background signal, indicating that the addition of further cleavage sites impart an increased activity to the system over and above what could have been expected, that was not foreseen nor suggested by the prior art.

In addition to the increase in activity, there seems to be an increase in specificity of the sequential cleavages by the NS3 protease. A recently emerging theory, based on in vitro structural studies of the HCV NS3 protease, is that the NS3 protease catalytic machinery is stabilized by specific substrates that contribute to enzyme activation through an induced-fit mechanism (Barbato et al., 2000, EMBO J., 19,1195–1206). The claims from this invention that an in vivo cell-based assay that incorporates multiple substrates, as presented in the context of a polyprotein, results in an NS3 protease with higher cell-based specific activity provide biological support for this theory.

Also, the level of expression of the polyprotein is so low with non-cytopathic expression systems, such as the CMV promoter, that one can not visualize the protein expressed (unless vaccinia virus expression system is used). It is therefore that much more surprising that such a low level of expression leads to such good detection of luciferase or SEAP.

REFERENCES

Ausubel et al., 1994, Current Protocols in Molecular Biology, Wiley, N.Y.
Barbato et al., 2000. EMBO J., 19, 1195–1206
Bartenschlager, R. et al., 1993, J. Virol., 67, 3835–3844.
Bartenschlager, R. et al., 1994, J. Virol., 68, 8147–8157.
Cho, Y. G. et al., 1997, J. Vir. Meth., 65, 201–207.
Cho, Y. G. et al., 1998, J. Vir. Meth., 72,109–115.
Elroy-Stein, O. and Moss, B. 1998, Current Protocols in Molecular Biology, Wiley, N.Y.
Griffiths and Page, 1994, Methods in Molec. Biol., 75, 427–440.
Gossen , M. and Bujard. H., 1992, Proc. Natl. Acad. Sci. USA., 89, 5547–5551.
Grakoui, A. et al., 1993(a), J. Virol. 67,1385–1395.
Grakoui A, et al., 1993(b), Proc Natl Acad Sci USA, 90, 10583–7
Hijikata, M. et al., 1991, Proc. Natl. Acad. Sci. USA. 88, 5547–5551.
Hijikata, M. et al, 1993, J. Virol. 67, 4665–4675.
Hirowatari, Y. et al., 1995, Anal. Biochem., 225, 113–220.
IUPAC-IUB Biochemical Nomenclature Commission, 1972, Biochemistry, 11, 1726–1732.
Kim, D. W. et al., 1995, Biochem. Biophys. Res. Comm., 215, 160–166.
Kim et al., 1999, Arch. Virol, 144, 329–343.
Kolykhalov et al., 1996, J. Virol., 70, 3363–3371,
Kwong A D. et al., 1998, Antiviral Res., 40, 1–18.
Lin, C. et al., 1994, J. Virol., 68, 8147–8157.
Llinas-Brunet, M. et al., 1998, Bioorganic & Med. Chem. Letters, 8, 2719–2724.
Lohmann et al., 1999, Science, 285, 110–113.
Love, R. A. et al., 1996, Cell, 87, 331–342.
Luckow. V. A., 1993, Curr. Op. Biotech., 4, 564–572.
Merrington et al., 1997, Molec. Biotech., 8(3), 283–297.
Overton, H. et al., 1995, J. Gen. Virol., 76, 3009–3019
Sambrook et al., 1989, Molecular Cloning—A Laboratory Manual, Cold Spring Harbor Labs.
Song et al, 1996, Mol. Cells, 6, 183–189.
Steinkuhler, C. et al., 1998. Biochemistry, 37, 8899–8905.
Tomei, L. et al., 1993, J. Virol., 67, 4017–4026.

What is claimed is:

1. A surrogate cell-based reporter system to evaluate the protease activity of Hepatitis C virus NS3 protease comprising a mammalian cell transfected with:

a) a first chimeric DNA molecule comprising:
  i) a non-cytopathic expression system for inducing expression of said first chimera upon transfection in said mammalian cell;
  ii) an HCV recombinant DNA molecule operably linked to said expression system, said HCV recombinant DNA molecule encoding an NS3–5 polyprotein comprising:
    an active NS3 protease,
    an NS4A protein, wherein the NS4A protein allows embedding of the polyprotein in the endoplasmic reticulum (ER) membrane and acts as a co-factor for the NS3 protease activity,
    NS4B and NS5A proteins of sufficient length to allow correct structural orientation of the active NS3 protease relative to an NS5A/5B target cleavage site, and
    NS5B protein or a fragment thereof sufficient to provide said NS5A/5B cleavage site for said active NS3 protease; and iii) a transactivator domain fused downstream of said HCV recombinant DNA molecule, said transactivator domain encoding a transactivator molecule capable of initiating expression of a reporter gene;
wherein said first chimeric DNA molecule encodes the polyprotein of SEQ ID NO:2; and
b) a second chimeric DNA molecule encoding said reporter gene co-joined to an operon responding to said transactivator molecule;
wherein expression of said first recombinant molecule leads to the production of a fusion polyprotein anchored to the endoplasmic reticulum of said mammalian cell, said fusion polyprotein being cleaved by said active NS3 protease thereby allowing translocation of said transactivator domain for inducing expression of said reporter gene as a means to evaluate said active NS3 protease activity.

2. The surrogate cell-based reporter system according to claim 1, wherein said NS3 protease is: (a) a NS3 protease truncated to exclude the helicase domain or (b) a NS3 protease wherein the helicase domain has been inactivated.

3. The surrogate cell-based reporter system according to claim 1, wherein said HCV recombinant DNA molecule comprises a nucleotide sequence coding for the full length NS3 polyprotein of HCV.

4. The reporter system according to claim 1, wherein said first chimeric DNA molecule comprises SEQ ID NO. 1.

5. The surrogate cell-based reporter system according to claim 1, wherein said first chimeric DNA molecule encodes the precursor polyprotein comprising all of the functional cleavage sites of: NS3/4A, 4A/4B, 4B/5A, and 5A/5B.

6. The surrogate cell-based reporter system according to claim 1, wherein said NS5A/5B cleavage site is cleavable by said active NS3 protease whereas one or more of the NS3/4A; 4A/4B; or 4B/5A cleavage sites is a variant not cleavable by said active NS3 protease.

7. The surrogate cell-based reporter system according to claim 1, wherein said non-cytopathic promoter system is selected from the group consisting of: a CMV (cytomegalovirus) promoter, a SV40 early-promoter system, and a RSV (Rous Sarcoma virus) LTR promoter system.

8. The surrogate cell-based reporter system according to claim 1, wherein said transactivator is selected from the group consisting of: tetracycline transactivator (tTA), NFκB, HIV-1 tat and GAL-4.

9. The surrogate cell-based reporter system according to claim 8, wherein said transactivator is tTA.

10. The surrogate cell-based reporter system according to claim 1, wherein said reporter gene encodes a molecule selected from the group consisting of: secreted alkaline phosphatase (SEAP), β-galactosidase, luciferase, chloramphenicol aminotransferase and green fluorescent protein.

11. The surrogate cell-based reporter system according to claim 10, wherein said reporter molecule is SEAP or luciferase.

12. The surrogate cell-based reporter system according to claim 11, wherein said reporter molecule is SEAP.

13. The surrogate cell-based reporter system according to claim 1, wherein said transactivator is tTA and said reporter is luciferase or secreted alkaline phosphatase (SEAP).

14. The surrogate cell-based reporter system according to claim 13, wherein said transactivator is tTA and said reporter is SEAP.

15. The surrogate cell-based reporter system according to claim 1, wherein said transactivator domain is located at the 3'-end of the first chimeric DNA molecule.

* * * * *